US011952622B2

(12) United States Patent
Feldman et al.

(10) Patent No.: US 11,952,622 B2
(45) Date of Patent: Apr. 9, 2024

(54) ANALYSIS OF DNA-CONTAINING SAMPLES AND RESOLUTION OF MIXED CONTRIBUTOR DNA SAMPLES

(71) Applicant: The Johns Hopkins University, Baltimore, MD (US)

(72) Inventors: Andrew B. Feldman, Columbia, MD (US); Jeffrey S. Lin, Silver Spring, MD (US); David Weitz, Bolton, MA (US); Assaf Rotem, Cambridge, MA (US)

(73) Assignee: The Johns Hopkins University, Baltimore, MD (US)

( * ) Notice: Subject to any disclaimer, the term of this patent is extended or adjusted under 35 U.S.C. 154(b) by 677 days.

(21) Appl. No.: 14/331,714

(22) Filed: Jul. 15, 2014

(65) Prior Publication Data
US 2015/0024378 A1    Jan. 22, 2015

Related U.S. Application Data

(60) Provisional application No. 61/847,683, filed on Jul. 18, 2013.

(51) Int. Cl.
*C12Q 1/68*     (2018.01)
*C12Q 1/6844*   (2018.01)
*C12Q 1/6869*   (2018.01)

(52) U.S. Cl.
CPC ......... *C12Q 1/6869* (2013.01); *C12Q 1/6844* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 8,137,912 B2 | 3/2012 | Kapur et al. | |
| 2007/0037185 A1* | 2/2007 | Coolbaugh-Murphy | C12Q 1/6827 435/6.11 |
| 2009/0132173 A1* | 5/2009 | Puch-Solis | G16B 20/00 702/19 |
| 2009/0215633 A1* | 8/2009 | Van Eijk | C12Q 1/6827 506/4 |
| 2010/0092973 A1* | 4/2010 | Davies | B01L 3/502784 435/6.19 |
| 2011/0118151 A1* | 5/2011 | Eshoo | C12Q 1/6844 506/39 |
| 2011/0159499 A1* | 6/2011 | Hindson | C12Q 1/6827 435/6.12 |
| 2012/0077730 A1* | 3/2012 | Haraldsson | C12N 15/1027 514/1.1 |
| 2012/0142088 A1 | 6/2012 | Hsiao et al. | |
| 2012/0164633 A1* | 6/2012 | Laffler | C12Q 1/6869 435/6.1 |
| 2013/0096011 A1 | 4/2013 | Rava et al. | |
| 2013/0109576 A1* | 5/2013 | Shuber | C12Q 1/6858 506/2 |
| 2013/0123120 A1 | 5/2013 | Zimmerman et al. | |
| 2013/0130919 A1* | 5/2013 | Chen | C12Q 1/6874 506/2 |
| 2013/0157871 A1* | 6/2013 | Jackson | C07K 1/22 506/2 |
| 2013/0225418 A1* | 8/2013 | Watson | G01N 1/30 506/2 |
| 2014/0011698 A1* | 1/2014 | Enzelberger | G01N 33/543 506/9 |

FOREIGN PATENT DOCUMENTS

| | | | | |
|---|---|---|---|---|
| WO | WO-2010018465 A2 * | 2/2010 | ........ | B01L 3/502784 |
| WO | WO-2013123125 A1 * | 8/2013 | ........... | C12Q 1/6851 |
| WO | WO-2013173394 A2 * | 11/2013 | ........... | C12Q 1/6869 |

OTHER PUBLICATIONS

Binladen J, Gilbert MT, Bollback JP, Panitz F, Bendixen C, Nielsen R, Willerslev E. The use of coded PCR primers enables high-throughput sequencing of multiple homolog amplification products by 454 parallel sequencing. PLoS One.Feb. 14, 2007; 2(2):e197.*
Cummings N, King R, Rickers A, Kaspi A, Lunke S, Haviv I, Jowett JB. Combining target enrichment with barcode multiplexing for high throughput SNP discovery. BMC Genomics. Nov. 18, 2010; 11:641, pp. 1-8.*
Diehl F, Li M, Dressman D, He Y, Shen D, Szabo S, Diaz LA Jr, Goodman SN, David KA, Juhl H, Kinzler KW, Vogelstein B. Detection and quantification of mutations in the plasma of patients with colorectal tumors. Proc Natl Acad Sci U S A. Nov. 8, 2005; 102(45):16368-73.*
Ehrich M, Deciu C, Zwiefelhofer T, Tynan JA, Cagasan L, Tim R, Lu V, McCullough R, Mccarthy E, Nygren AO, Dean J, Tang L, Hutchison D, Lu T, Wang H, Angkachatchai V, Oeth P, Cantor CR, Bombard A, van den Boom D. Noninvasive detection of fetal trisomy 21 by sequencing of DNA in maternal blood: a study in a clinical setting. Am J Obstet Gynecol. 2011.*
Kumaresan P, Yang CJ, Cronier SA, Blazej RG, Mathies RA. High-throughput single copy DNA amplification and cell analysis in engineered nanoliter droplets. Anal Chem. May 15, 2008; 80(10):3522-9.*

(Continued)

*Primary Examiner* — Samuel C Woolwine
*Assistant Examiner* — Olayinka A Oyeyemi

(57) ABSTRACT

Methods for analyzing DNA-containing samples are provided. The methods can comprise isolating a single genomic equivalent of DNA from the DNA-containing sample to provide a single isolated DNA molecule. The single isolated DNA molecule can be subjected to amplification conditions in the presence of one or more sets of unique molecularly tagged primers to provide one or more amplicons. Any spurious allelic sequences generated during the amplification process are tagged with an identical molecular tag. The methods can also include a step of determining the sequence of the one or more amplicons, in which the majority sequence for each code is selected as the sequence of the single original encapsulated target. The DNA-containing sample can be a forensic sample (e.g., mixed contributor sample), a fetal genetic screening sample, or a biological cell.

18 Claims, 12 Drawing Sheets

Specification includes a Sequence Listing.

(56) References Cited

OTHER PUBLICATIONS

Galbiati S, Smid M, Gambini D, Ferrari A, Restagno G, Viora E, Campogrande M, Bastonero S, Pagliano M, Calza S, Ferrari M, Cremonesi L. Fetal DNA detection in maternal plasma throughout gestation. Hum Genet. Jul. 2005; 117(2-3):243-8.*
Lo YM, Tsui NB, Chiu RW, Lau TK, Leung TN, Heung MM, Gerovassili A, Jin Y, Nicolaides KH, Cantor CR, Ding C. Plasma placental RNA allelic ratio permits noninvasive prenatal chromosomal aneuploidy detection. Nat Med. Feb. 2007; 13(2):218-23.*
Lo YM, Chan KC, Sun H, Chen EZ, Jiang P, Lun FM, Zheng YW, Leung TY, Lau TK, Cantor CR, Chiu RW. Maternal plasma DNA sequencing reveals the genome-wide genetic and mutational profile of the fetus. Sci Transl Med. Dec. 8, 2010; 2(61):61ra91. pp 1-15.*
Pekin D, Skhiri Y, Baret JC, Le Corre D, Mazutis L, Salem CB, Millot F, El Harrak A, Hutchison JB, Larson JW, Link DR, Laurent-Puig P, Griffiths AD, Taly V. Quantitative and sensitive detection of rare mutations using droplet-based microfluidics. Lab Chip. Jul. 7, 2011; 11(13):2156-66.*
Pekin et al. Supplementary information. Lab Chip. Jul. 7, 2011; 11(13):2156-66.*
Smith AM, Heisler LE, St Onge RP, Farias-Hesson E, Wallace IM, Bodeau J, Harris AN, Perry KM, Giaever G, Pourmand N, Nislow C. Highly-multiplexed barcode sequencing: an efficient method for parallel analysis of pooled samples. Nucleic Acids Res. Jul. 2010; 38(13):e142, pp. 1-7.*
Xu MY, Aragon AD, Mascarenas MR, Torrez-Martinez N, Edwards JS. Dual primer emulsion PCR for next-generation DNA sequencing. Biotechniques. May 2010; 48(5):409-12.*
Van den Oever JM, Balkassmi S, Verweij EJ, van Iterson M, Adama van Scheltema PN, Oepkes D, van Lith JM, Hoffer MJ, den Dunnen JT, Bakker E, Boon EM. Single molecule sequencing of free DNA from maternal plasma for noninvasive trisomy 21 detection. Clin Chem. Apr. 2012; 58(4):699-706.*
Van den Oever JM, Balkassmi S, Johansson LF, Adama van Scheltema PN, Suijkerbuijk RF, Hoffer MJ, Sinke RJ, Bakker E, Sikkema-Raddatz B, Boon EM. Successful noninvasive trisomy 18 detection using single molecule sequencing. Clin Chem. Apr. 2013; 5 9(4):705-9.*
Chubiz LM, Lee MC, Delaney NF, Marx CJ. FREQ-Seq: a rapid, cost-effective, sequencing-based method to determine allele frequencies directly from mixed populations. PLoS One. 2012; 7(10): e47959. pp. 1-9. Epub Oct. 31, 2012. (Year: 2012).*
Binladen J, Gilbert MT, Bollback JP, Panitz F, Bendixen C, Nielsen R, Willerslev E. The use of coded PCR primers enables high-throughput sequencing of multiple homolog amplification products by 454 parallel sequencing. PLoS One.Feb. 14, 2007; 2(2):e197. pp. 1-9. (Year: 2007).*
Gabriel C, Danzer M, Hackl C, Kopal G, Hufnagl P, Hofer K, Polin H, Stabentheiner S, Pröll J. Rapid high-throughput human leukocyte antigen typing by massively parallel pyrosequencing for high-resolution allele identification. Hum Immunol. Nov. 2009; 70(11):960-4. Epub Aug. 23, 2009. (Year: 2009).*
Fu, G.K., Hu, J., Wang, p. H. and Fodor, S.P., 2011. Counting individual DNA molecules by the stochastic attachment of diverse labels. Proceedings of the National Academy of Sciences, 108(22), pp. 9026-9031. (Year: 2011).*
Burnham et al., 2011. AIC model selection and multimodel inference in behavioral ecology: some background, observations, and comparisons. Behavioral ecology and sociobiology, 65, pp. 23-35. (Year: 2011).*
Chan et al., Detection of paternal alleles in maternal plasma for non-invasive prenatal diagnosis of beta-thalassemia: A feasibility study in southern Chinese. Eur J Obstet Gynecol Reprod Biol. 2010; 150: 28-33. (Year: 2010).*
Devaney et al., 2011. Noninvasive fetal sex determination using cell-free fetal DNA: a systematic review and meta-analysis. JAMA, 306(6), pp. 627-636. (Year: 2011).*
Pinheiro et al., 2012 Evaluation of a droplet digital polymerase chain reaction format for DNA copy number quantification. Anal Chem, 84:1003-11. (Year: 2012).*
Snyder et al., 2011. Universal noninvasive detection of solid organ transplant rejection. Proceedings of the National Academy of Sciences, 108(15), pp. 6229-6234. (Year: 2011).*
Tong et al., (2006). Noninvasive prenatal detection of fetal trisomy 18 by epigenetic allelic ratio analysis in maternal plasma: Theoretical and empirical considerations. Clinical Chemistry, 52(12), 2194-2202. (Year: 2006).*
Van den Oever., 2013. Successful noninvasive trisomy 18 detection using single molecule sequencing. Clinical Chemistry, 59(4), pp. 705-709. (Year: 2013).*
Zimmermann et al., (2012). Noninvasive prenatal aneuploidy testing of chromosomes 13, 18, 21, X, and Y, using targeted sequencing of polymorphic loci. Prenatal Diagnosis, 32(13), 1233-1241. (Year: 2012).*
Kenneth P. Burnham et al., "Model Selection and Multimodel Inference," Second Edition, Springer, 2002, pp. 60-79.

* cited by examiner

Error Sources to be eliminated:

PCR stutter products

PCR Chimeras (template switching)

Sequencer base calling errors

PCR substitution errors

Allele quantitation bias

Person 1  TTATTATTATTATTATTATTATTATTATTATT  ; SEQ ID NO:1

Allele 11 = 11 TAT Repeats

Person 2  TTATTATTATTATTATTATTATTATTATTATTATTATT  ; SEQ ID NO:2

Allele 13 = 13 TAT Repeats

Y Chromosome STR Locus DYS392

RATIO 2:1

FIGURE 7

FIGURE 9

ANALYSIS OF DNA-CONTAINING SAMPLES AND RESOLUTION OF MIXED CONTRIBUTOR DNA SAMPLES

SEQUENCE LISTING

The instant application contains a Sequence Listing which has been submitted electronically in ASCII format and is hereby incorporated by reference in its entirety. Said ASCII copy, created on Aug. 13, 2014, is named 39217-09073_SL.txt and is 668 bytes in size.

TECHNICAL FIELD

The presently disclosed invention relates generally to methods of analyzing DNA-containing samples, such as forensic samples, fetal genetic screening samples, or biological cellular, bacterial, or viral samples. The presently disclosed invention, in accordance with certain embodiments, enables determination of error-free single DNA molecule or RNA molecule sequences from such samples. This disclosed invention may be suitable for identifying the total number of contributors in mixed-contributor samples, quantifying the proportion of each of the respective contributors, forming genotypes from DNA sequences over a set of forensic genetic loci, early identification of chromosomal abnormalities, such as anueploidy during fetal genetic screening in maternal blood sera, and characterization of cellular abnormalities within biological cellular samples, such as cancerous cells in heterogeneous mixed cell populations.

BACKGROUND

The forensic field is constantly striving for more rapid, robust and sensitive methods to perform DNA genotyping. As the molecular techniques available to forensic scientists have become more sensitive, the ability to detect minor contributors in mixture samples has increased. Resolving mixtures with high sensitivity and certainty, however, remains an outstanding problem in the human forensic genetics field.

The main strategy now used to analyze DNA mixtures is a combination of differential extraction (i.e., separating different cells prior to genotyping) and computational analysis of the allele peak heights in capillary electropherograms (EPGs). EPGs genotypes are based on the lengths of alleles (the number of DNA bases in the DNA strand) for each forensic locus of interest. Commercial mixture analysis software tools based on EPG data characteristics are now coming into use, however, they are currently limited to analysis of allele length versus allele sequences, and are required to make specific assumptions to represent the unknowable and specimen-specific amplification and sequencing noise process that produces spurious (false) content in the end-to-end sample analysis.

Currently, a major obstacle to resolving mixed contributor samples, and attaining the certainty of resolution required in courts of law (and required for taking high regret actions), is the spurious sequence content introduced into a sample analysis by the DNA amplification and the second generation DNA sequencer system base calling error process. This content currently limits resolution of minor contributors to those greater than about 5% of total sample DNA, even when using next generation DNA sequencing data rather than EPG data.

Accordingly, there remains a need for methods of providing DNA-containing sample preparation and analysis that significantly, if not completely, eliminates all noise sources, and can enable minor contributor detection down to the 1/1000 level and beyond in a typical second generation DNA sequencing run with 5M-10M sequencer reads, such as the Illumina MiSeq. This sensitivity is only limited by the chosen depth of the second generation sequencing run.

BRIEF SUMMARY

One or more embodiments of the present invention may address one or more of the aforementioned remaining needs. For instance, certain embodiments according to the present invention provide methods of providing DNA-containing sample preparation and analysis that significantly, if not completely, eliminates all noise sources, and can enable minor contributor detection down to the 1/1000 level in a single MiSeq analysis at, for example, 10 forensic genetic loci. In general, certain embodiments of the present invention can facilitate such an achievement, in part, by isolating single molecules prior to amplification and then applying a primer "bar-coding" (a unique string of nucleic acid bases) scheme to produce an error-free sequence of each molecule based on informatic analysis of post-amplification sequences of the data. A mixed sample, therefore, can be resolved one contributor molecule at a time.

In one aspect, embodiments of the present invention provide methods of analyzing a DNA-containing sample, such as a mixed-contributor sample, including a step of isolating a single genomic equivalent of DNA from the DNA-containing sample to provide a single isolated target DNA molecule. The single isolated DNA molecule can be subjected to amplification conditions in the presence of one or more sets of unique DNA bar-coded (e.g., molecularly tagged) primers to provide one or more amplicons, in which all spurious allelic sequences generated during the amplification process are tagged with an identical DNA barcode. In accordance with certain embodiments, the sequences of the one or more amplicons can be determined, in which the majority sequence for each code is selected as the sequence of the single original encapsulated target DNA molecule.

According to certain embodiments of the present invention, the step of isolating a single genomic equivalent of DNA comprises forming at least one liquid droplet encapsulating the single genomic equivalent of DNA or less from the DNA-containing sample. In certain embodiments, the at least one liquid droplet is formed via a droplet microfluidic device. In certain embodiments, the droplet containing the DNA sample is co-located with the barcoded amplification primer in the same reaction vessel (droplet) using a microfluidic device that performs droplet merging, performs co-encapsulation via co-flowing, or is achieved by injecting either the barcoded primers or the DNA into the droplet containing the other reaction component.

According to certain embodiments of the present invention, the barcoded primers are fixed onto single polystyrene beads or other similar substrates/surfaces.

According to certain embodiments of the present invention, the proportion of each contributor's DNA can be determined by averaging the estimation proportions of error-free DNA sequences over the set of genomic loci analyzed in the experiment and the uncertainty in this value can be strictly determined based on each locus proportion obeying Poisson counting statistics.

According to certain embodiments of the present invention, the proportions of each of the contributor's DNA inference at each forensic locus can be used to form complete genotypes using an algorithm that does not require prior assumptions regarding the actual number of contributors present in the sample.

BRIEF DESCRIPTION OF THE DRAWING(S)

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements Like numbers refer to like elements throughout.

FIG. 7 depicts the noise sources to be eliminated via one embodiment of the present invention as applied to a 2 person mixture of 2 males using a Y-chromosome forensic genetic locus. FIG. 7 discloses SEQ ID NOS 1-2, respectively, in order of appearance.

FIG. 9 shows representative results for 20 barcodes of allele counts broken out by barcode sequence following application of the method according to certain embodiments of the present invention, but prior to bioinformatics analysis applied to the sequencer reads.

DETAILED DESCRIPTION

Figure 1:
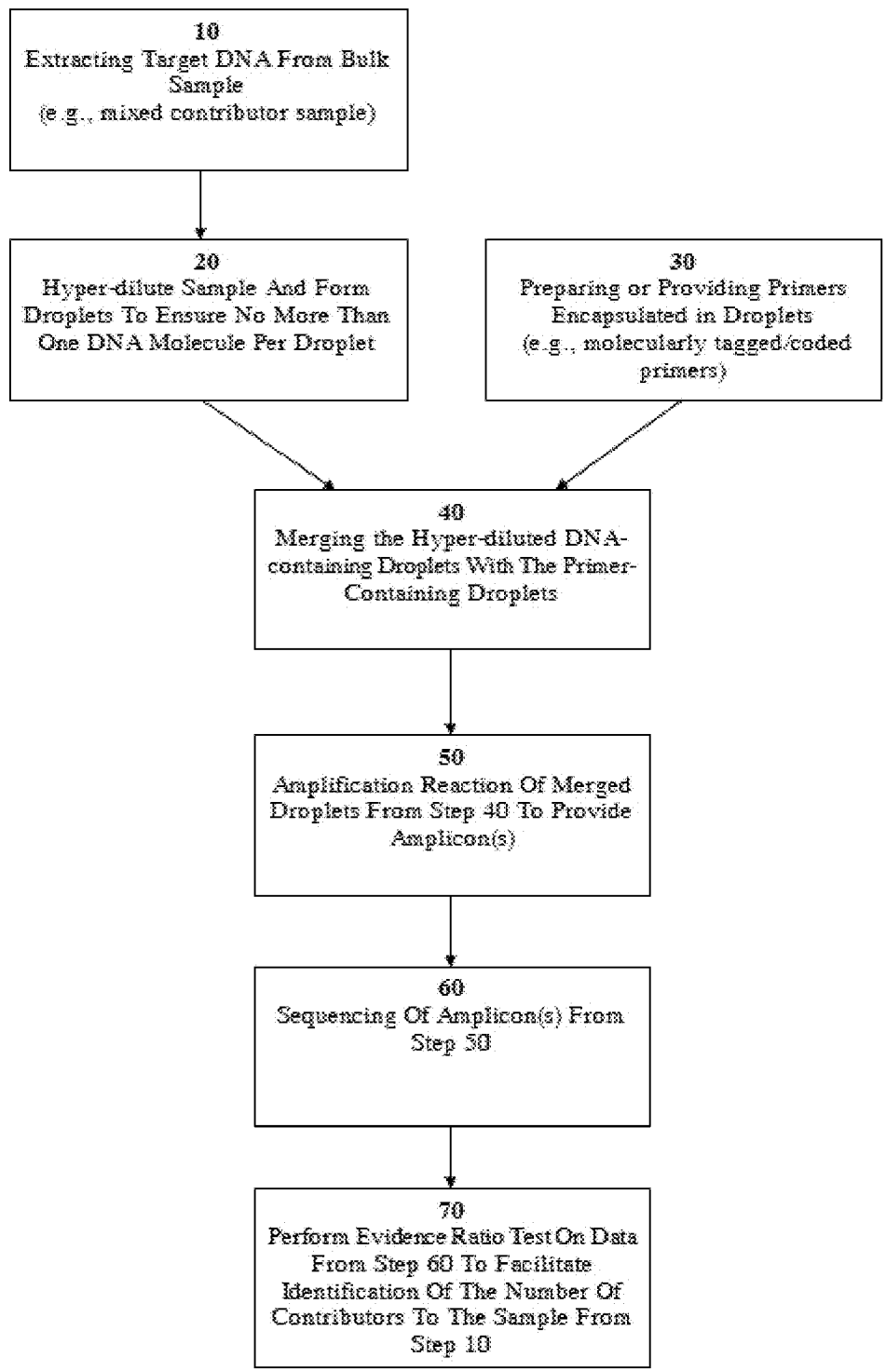
FIG. 1 is a flow diagram illustrating certain embodiments according to the present invention.

The present invention now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, the term DNA refers to polymer molecules that encode information, in some embodiments DNA and RNA, that can be amplified, through biomolecular processes, such as polymerase chain reaction (PCR) or transcription, using natural or artificially engineered or synthetically produced molecular enzymes or catalysts, and that can be analyzed to determine the approximate or exact sequence, or composition of polymer subunits.

As used herein, the term "DNA-containing sample", as used herein, can comprise any composition including DNA and capable of being analyzed by methods provided herein. In certain embodiments, the sample comprises or is suspected to comprise DNA from one or more contributors (e.g., individuals). Samples can comprise "mixed" samples or a "mixture", in which these terms can refer to samples containing DNA from one or more contributors. In accordance with certain embodiments, that is, the mixed contributor sample can include DNA from an unknown number of individual contributors prior to analysis of the sample according to certain embodiments of the present invention. Exemplary, non-limiting, samples include forensic samples, biological cells, and fetal genetic screening samples. In some embodiments, the sample comprises a mother's blood serum including fetal DNA therein, in which the sample (e.g., mother's blood serum) can be taken from the mother from at least any of the following: 2, 3, 4, 5, and 6 weeks gestation and/or at most about any of the following: 8, 12, 20, and 40 weeks gestation (e.g., 4-8 weeks gestation, 3-5 weeks gestation, etc.).

The term "droplet", as used herein, can comprise a small volume of liquid which is immiscible with its surroundings (e.g., gases, liquids, surfaces, etc.). A droplet may reside upon a surface, be encapsulated by a fluid with which it is immiscible (e.g., the continuous phase of an emulsion), or a combination thereof. A droplet can typically comprise a spherical or substantially spherical shape, but can be non-spherical. The volume of a droplet and/or the average volume of a set or plurality of droplets provided herein can comprise less than about one microliter. Droplet volumes, in accordance with certain embodiments can range from picoliter to nanoliter range, including all sub-ranges therein, but are not necessarily limited to this range. The diameter of a droplet and/or the average diameter of a set or plurality of droplets provided herein can comprise less than about one millimeter, for example in the 1-100 micron diameter range, but are not necessarily limited to this range. Droplets may be monodisperse (e.g., substantially monodisperse) or polydisperse.

As used herein, the terms "amplify", "amplifying" or "amplification" in the context of DNA can comprise the production of multiple copies of a targeted DNA sequence or a portion thereof, typically starting from a small amount of the DNA (e.g., a single DNA molecule), where the amplification products or amplicons are generally detectable. Amplification of targeted DNA sequences can encompass a variety of chemical and enzymatic processes. The generation of multiple DNA copies from one or a few copies of a target or template DNA molecule (or portion thereof) during a polymerase chain reaction (PCR) or a ligase chain reaction (LCR) can comprise forms of amplification.

As used herein, the term "primer" comprises an oligonucleotide or its equivalent for the targeted polymer, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of DNA and an inducing agent such as a biocatalyst (e.g., a DNA polymerase or the like) and at a suitable temperature and pH)). In certain embodiments, the primer is typically single stranded for maximum efficiency in amplification, but may alternatively be double stranded. If double stranded, the primer can be first treated to separate its strands before being used to prepare extension products. In certain embodiments the primer is affixed to the surface of a bead of similar substrate. In certain embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method.

As used herein, the term "single genomic equivalent" comprises the amount of DNA necessary to be present in a sample to guarantee that all genes will be present. This number increases with the total genome size of an organism and can be calculated by converting the size of a genome in base pairs to micrograms of DNA.

In one aspect, certain embodiments according to the present invention provide methods of providing DNA-containing sample preparation and analysis that significantly, if not completely, eliminates all noise sources from amplification and subsequent sequencing, and can enable minor contributor detection down to at least the 1/1000 level in a single MiSeq analysis. In general, certain embodiments of the present invention can facilitate such an achievement, in part, by isolating single molecules prior to amplification and then applying a barcode comprising or consisting of an oligonucleotide sequence to the amplification primer to produce an error-free sequence of each molecule from analysis, for example, of MiSeq data. A mixed sample, therefore, can be resolved one error-free contributor molecule at a time.

For instance, certain embodiments of the present invention can present a beneficially profound impact on removal of confounding spurious sequence content in mixed samples. Five major noise sources for the reliable identification minor DNA-contributors in mixed samples, for example, can be significantly reduced or completely eliminated according to certain embodiments of the present invention. The primary noise source, the phenomenon called "stutter", is the most confounding. For instance, most current forensic loci of interest are tandem stretches of short repeating sequences (e.g., 3, 4, 5 bases long) called short tandem repeats (STRs). The alleles differ in the number of repeats and generally vary between people, but are shared at a certain frequency in a given population of individuals. When STRs are amplified, slippage occurs during annealing of DNA during thermal cycling, which produces spurious alleles with repeat numbers both above and below the original target molecule. This spurious content mimics the presence of a minor contributor, and is the major source of sensitivity loss in mixture analysis (e.g., analysis of samples containing multiple DNA contributors) that the above embodiments of the present invention address. The second noise source is a phenomenon called template switching. In mixture samples, the amplification enzyme can jump from one template to the other and thereby create chimeric alleles mimicking a new contributor with sequence content from more than one template. A third source is erroneous base incorporation during the template extension process, which produces spurious content, in this case false single nucleotide polymorphisms (SNPs). A fourth source is the base calling errors of the sequencer system, which also produces false SNPs. Finally, while not a source of spurious content, biases in target amplification due thermodynamic and other factors that vary with allele length and base composition cause uncertainties in quantification of proportion values for the minor and major contributors, a critical parameter needed to resolve the mixture across forensic genomic loci. Embodiments according to certain embodiments of the present invention can significantly reduce or eliminate one or more (e.g., all) of the foregoing noise sources and, thus, removal of spurious sequence content.

In accordance with certain embodiments, the present invention provides methods of analyzing a DNA-containing sample, such as a mixed-contributor sample, including a step of isolating a single genomic equivalent or less of DNA from the DNA-containing sample to provide a single isolated DNA molecule. The single isolated DNA molecule can be subjected to amplification conditions in the presence of one or more sets of unique barcoded primers to provide one or more amplicons, in which all spurious allelic sequences generated during the amplification process are tagged with an identical barcode. In accordance with certain embodiments, the sequences of the one or more amplicons can be determined, in which the majority sequence for each code is selected as the sequence of the single original encapsulated target.

In accordance with certain embodiments of the present invention, the step of isolating a single genomic equivalent of DNA comprises forming at least one liquid droplet encapsulating the single genomic equivalent of DNA from the DNA-containing sample. The DNA-containing sample can contain DNA from a single contributor or from multiple contributors, in which the actual number of contributors (e.g., 1, 2, 3, etc.) is unknown prior to analysis according to certain embodiments of the present invention. For mixed contributor samples, for example, the mixture of DNA sequences contained in the sample will not allow direct sequencing of the DNA to provide a reliable or accurate resolution of the individual DNA sequences contained therein. In accordance with certain embodiments, therefore, the sample can be processed into a plurality of liquid droplets formed via a droplet microfluidic device. Such devices are used in products developed by, for example, Dolomite.

The microfluidic-based approach, according to certain embodiments of the present invention, can eliminate each and every one of the above sources of spurious content and quantitative bias. For example, DNA molecules will be isolated to no more than a single genome equivalent into single droplets using an encapsulating droplet microfluidic device. Primers for the amplification reaction can be synthesized (or provided) and encapsulated in droplets, according to certain embodiments of the present invention, with each primer containing, for example, a unique 8-nucleotide sequence code for all primers, and optionally with primer code sequences varying between droplets. In accordance with certain embodiments, an associated pair of primers within a drop may contain the same code or may contain different codes. The primer-containing droplets can then be merged with genome-containing droplets using a microfluidic droplet-merging device. Alternatively, the co-location of the target DNA molecule and primer in the droplet can be achieved by co-flowing them and co-encapsulating them into single droplets. The joined/merged droplets can then be collected and in-droplet thermal cycling can be performed on each simultaneously. Each molecule of the amplified product in each drop will now be tagged with, for example, a unique 8-letter code. Importantly, all the spurious allelic sequences generated during the amplification process are tagged with that identical code. Following sequencing, the majority sequence for each code is selected, as it will represent the sequence of the single original encapsulated target. Since all targets were segregated prior to amplification (e.g., only a single DNA molecule within a single droplet ensures amplification performed on DNA from a single contributor per droplet), all chimeric content will be eliminated as well. Finally, while the biases in amplification for different alleles will yield variable quantities of DNA product per target, the collapsing of the amplified output to a single original target for each code completely eliminates this bias. Counts of individual coded target molecules in a sample will thus follow a simple Poisson counting statistical model—a well-characterized distribution that will enable resolution of a mixed sample with the highest accuracy possible. The counts of major and minor contributor molecules are, for example, used to determine the proportion of, for example, the fetal DNA components of DNA extracted from maternal blood sera. This is a critical parameter in determining the over-representation of fetal chromosomes in specific aneuploidies with diagnostic values, such as Chromosome 21 (Down's Syndrome).

The plurality of liquid droplets, according to certain embodiments, can comprise a first group of liquid droplets containing zero genomic equivalents of DNA and a second group of liquid droplets containing only one genomic equivalent of DNA. In this regard, the plurality of liquid droplets can comprise an average of less than one genomic equivalent of DNA per individual liquid droplet. In some embodiments, each partition contains zero or one nucleic acid molecules. In accordance with certain embodiments, the step of isolating a single genomic equivalent of DNA comprises hyper-diluting the DNA-containing sample and forming at least one liquid droplet encapsulating the single genomic equivalent of DNA from the DNA-containing sample, in which some of the liquid droplets are devoid of any DNA. In certain embodiments, the bulk sample is hyper-diluted and formed into a plurality of liquid droplets in such a manner to reduce the likelihood (e.g., approaching zero likelihood) of any droplet containing two or more DNA molecules. The volume and number of droplets can be varied and based, at least in part, on the total bulk sample volume and concentration of DNA present in the bulk sample in order to ensure zero or one nucleic acid molecules per individual liquid droplet.

In accordance with certain embodiments, the step of hyper-diluting the DNA-containing sample comprises diluting the DNA-containing sample such that about one liquid droplet for every 50 to 150 liquid droplets includes an isolated single genomic equivalent of DNA. In certain embodiments, a single DNA molecule can be present in a single liquid droplet per at least any of the following: 5, 15, 25, 50, 75, 100, 125, 150, 175, or 200 droplets (e.g., single DNA molecule in a single droplet per every 5-200 droplets produced).

Methods according to certain embodiments of the present invention also utilize one or more sets of unique molecularly tagged primers to provide one or more amplicons (e.g., amplification of targeted DNA sequence(s)), in which all spurious allelic sequences generated during the amplification process are tagged with an identical molecular code. In accordance with certain embodiments, the one or more sets of unique molecularly tagged primers can be encapsulated within liquid droplets formed via a droplet microfluidic device. In certain embodiments, each of the one or more sets of unique molecularly tagged primers is configured to amplify a different set of target amplicons. For example, a first set of primers can be molecularly tagged with a first code and configured to amplify a first targeted DNA sequence and second set of primers can be molecularly tagged with a second (and different) code and configured to amplify a second (and different) targeted DNA sequence. In accordance with certain embodiments of the present invention, the primers can be affixed to polystyrene beads or similar substrates.

In certain embodiments, the liquid droplets formed via a droplet microfluidic device encapsulating one or more sets of unique molecularly tagged primers comprises a plurality of sets of molecularly tagged primers encapsulated within each droplet. For instance, each droplet can comprise a first primer set comprising a first molecular tag and a second primer set comprising a second molecular tag, in which the first molecular tag is different than the second molecular tag and the first primer set and second primer set each target a different DNA sequence. In this regard, each set of molecularly tagged primers can comprise a unique, respective molecular tag or code.

In accordance with certain embodiments, the liquid droplets formed via a droplet microfluidic device encapsulating one or more sets of unique molecularly tagged primers comprises a plurality of liquid droplets in which each liquid droplet includes only a single set of primers, in which the liquid droplets include a first group of liquid droplets containing a first primer set comprising a first molecular tag or code and a second group of liquid droplets containing a second primer set comprising a second molecular tag or code. In such embodiments, the first molecular tag or code is different than the second molecular tag or code and the first and second primer sets are each configured to amplify a different DNA sequence.

Methods according to certain embodiments of the present invention can comprise a step of merging DNA-containing liquid droplets with primer-containing droplets to provide one or more merged-droplets, or co-location of DNA target with primer via co-flow encapsulation into a single droplet. The merged-droplets comprise a single genomic equivalent of DNA from the DNA-containing sample and one or more sets of the unique molecularly tagged/coded primers. The merged-droplets can be subjected to amplification conditions to provide one or more amplicons of one or more targeted DNA sequences. In certain embodiments, the step of merging the DNA-containing liquid with primer-containing liquid can be performed with a microfluidic device configured for co-flowing into a single droplet. Such devices are available by Dolomite, for example.

In accordance with certain embodiments, the single isolated DNA molecule(s) (e.g., a first isolated DNA molecule in a first liquid droplet and a second, different isolated DNA molecule in a second liquid droplet) can be subjected to amplification conditions in the presence of the one or more sets of unique molecularly tagged primers to provide one or more amplicons, in which all spurious allelic sequences generated during the amplification process are tagged with an identical molecular tag. In certain embodiments, amplification can be performed on a sample that has been divided into the liquid droplets. The amplification reaction can be carried out within each droplet. In such instances, each droplet containing DNA also contains all the reagents necessary for amplification of targeted DNA sequences. For instance, the amplification reaction can be carried out for the one or more liquid droplets containing (i) a single genomic equivalent of DNA from the DNA-containing sample and (ii) one or more sets of unique molecularly tagged primers.

In certain embodiments, an amplification reaction can comprise any reaction in which targeted DNA (or a portion thereof) replication occurs repeatedly over time to form multiple copies of at least one segment of a template or target DNA (or portion thereof). In some embodiments, amplification generates an exponential or linear increase in the number of copies of the template DNA. Amplifications may produce in excess of a 1,000-fold increase in template copy-number and/or target-detection signal. Exemplary amplification reactions include, but are not limited to, polymerase chain reaction (PCR) or ligase chain reaction (LCR), each of which is driven by thermal cycling. Alternative amplification reactions, which may be performed isothermally, may also find use herein, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like.

Amplification may be performed with any suitable template DNA, primers, probes, buffers, replication catalyzing enzyme (e.g. DNA polymerase), nucleotides, salts (e.g. $MgCl_2$), etc. In certain embodiments, an amplification mixture can include any combination of at least one primer or primer pair (set of primers), at least one probe, at least one replication enzyme (e.g., at least one polymerase, such as at least one DNA polymerase), and deoxynucleotide (and/or nucleotide) triphosphates (dNTPs and/or NTPs), etc.

In certain embodiments, methods of the present invention can utilize amplification that relies on alternating cycles of heating and cooling (i.e., thermal cycling) to achieve successive rounds of replication (e.g., PCR). In certain embodiments, PCR is used to amplify targeted DNA sequences. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. Typical PCR methods produce an exponential increase in the amount of a product amplicon over successive cycles, although linear PCR methods also find use in the present invention.

The resulting amplicons, each molecularly tagged with a unique code, can then be subjected to sequencing process. In certain embodiments, any suitable systems, devices, compositions, and methods for nucleic acid sequence analysis are within the scope of certain embodiments of the present invention. Non-limiting examples of nucleic acid sequencing techniques include, but are not limited to, chain terminator (Sanger) sequencing and dye terminator sequencing, as well as "second generation" sequencing techniques.

The so-called "second-generation sequencing" or "next-generation sequencing" (NGS) techniques have emerged as alternatives to Sanger and dye-terminator sequencing methods and can by beneficially utilized in certain embodiments according to the present invention. NGS methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing, template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence. In accordance with certain embodiments of the present invention, the methods of the present invention utilize pyrosequencing.

In the Solexa/Illumina platform (e.g., MiSeq sequencing platform), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run. In accordance with certain embodiments of the present invention, the methods of the present invention utilize the Solexa/Illumina approach discussed above.

The data obtained from the sequencing procedure, can be analyzed in a variety of manners for identification of specific amplicons present in the sample as well as identification of the number or contributors in a mixed sample. The sequencing data can also be used to identify chromosomal abnormalities in fetal genetic screening applications and analysis of biological cells (e.g., tumor cells) for characterization and treatment.

FIG. 1 is a flow diagram illustrating certain embodiments according to the present invention. As shown in FIG. 1, the bulk sample containing DNA can be processed by extracting target DNA 10 from the bulk sample followed by hyperdiluting the sample and forming a plurality of droplets 20 in a manner such that no more than 1 DNA target molecule is present per single liquid droplet. A step of providing or preparing one or more sets of primers 30, as discussed above, in which the primers are encapsulated in liquid droplets can be performed. Methods represented by FIG. 1, illustrate a merging step 40, in which DNA-containing droplets are merged with primer-containing droplets to provide merged-droplets containing both DNA from the sample and primers for amplification. Steps 20, 30, and 40, can alternatively be achieved through a co-flow device arrangement that encapsulates both the DNA target and the primer or bead with affixed primer into a single droplet by controlling the relative flow rates. The merged-droplets are next subjected to an amplification reaction 50 to provide one or more amplicons of interest. After the amplification reaction 50 has been completed, the amplicons can undergo a sequencing process 60. The final step illustrated in FIG. 1 comprises subjecting the sequencing data from the sequencing process 60 to an Evidence Ratio test, as discussed below, to identify the number of contributors in the bulk sample and form genotypes from the processed sequence data across the multiple loci analyzed.

In certain embodiments related, for example, to forensic samples, the number of contributors in a mixed contributor sample can be readily identified by performing an Evidence Ratio analysis as discussed in greater detail below. The Evidence Ratio analysis approach beneficially is not dependent upon an initial assumption as to the number of contributors present in a mixed sample. The present approach, according to certain embodiments, allows the number of contributors in the model to be inferenced based on the weight of the evidence, rather than assumed a priori. Such methods beneficially reduce the risk of false exclusion and false detection of genotypes in mixed samples due to potential under- and over-fitting of the model to the data.

Computation of Likelihood Ratios for Mixed Contributor DNA Profiles

We begin the development using the formula for the continuous Likelihood Ratio ($LR_c$) for the alternative hypotheses of the defense and the prosecution used in the commercial STRMix DNA mixture analysis program [1]. In this computation, the evidence $G_c$ is derived from electropherogram data and comprises the set of detected alleles over the specific set L of the forensic loci used in the analysis. The likelihood ratio is derived by considering the two alternatives hypotheses $H_1$ and $H_2$, corresponding to those typical for the prosecution and defense, respectively, in a criminal case. The person of interest (POI) is assumed to be present under $H_1$, but not under $H_2$. Each genotype set under $H_1$ must contain the genotype of the POI. Genotype sets defined for $H_2$ may or may not contain the POI. The likelihood ratio $LR_c$ is the probability of observing the evidence $G_c$ under hypotheses $H_1$ divided by the probability of observing the evidence $G_c$ under $H_2$: $LR_c = Pr(G_c|H_1)/Pr(G_c|H_2)$. For each hypothesis there are J specific genotype sets $\{S_j: j=1, \ldots J\}$ that could plausibly explain the observed data. Expanding the expressions for $Pr(G_c|H)$ over potential explanatory genotype sets gives the following expression [1]:

$$LR_c = \frac{\sum_j Pr(G_c|S_j)Pr(S_j|H_1)}{\sum_{j'} Pr(G_c|S_{j'})Pr(S_{j'}|H_2)}. \quad \text{Eq. (1)}$$

For each genotype set $S_j$ there are a number of underlying parameters that are used to describe the DNA profile. In reference [1], these are termed mass parameters, and include a template DNA amount for each contributor in a mixed sample, a degradation level for each contributor, amplification efficiency for each locus, and an accounting for spurious allelic content due to stutter. A genotype set and its associated mass parameters constitute a specific "model" of the data, with the model's parameter values derived from a fitting procedure that assumes a specific statistical model of the experimental noise in measuring $G_c$. The quantity $Pr(G_c|S_j)$ in Eq. (1) is the likelihood of observing the data $G_c$ given the fitted model for given genotype set $S_j$. This "goodness-of-fit" value provides a weighting for each of the genotypes population frequencies $Pr(S_j|H)$ in $LR_c$. In reference [1], this interpretation of the likelihood is made explicit by re-writing Eq. (1) as:

$$LR_c = \frac{\sum_j w_j Pr(S_j|H_1)}{\sum_{j'} w_{j'} Pr(S_{j'}|H_2)}. \quad \text{Eq. (2)}$$

The probability terms $Pr(S_j|H_1)$ and $Pr(S_j|H_2)$ in Eqs. (1) and (2) are the population frequencies of the genotypes, the calculation of which has been well treated elsewhere. Thus, the problem to be solved is computing the goodness-of-fit weightings $w_j$ and $w_{j'}$. In reference [1], the weightings are determined through a statistical sampling procedure call a Markov Chain Monte Carlo (MCMC). The authors acknowledge that such methods will produce a variable result each time the method is applied to identical evidentiary data, but their reproducibility analysis showed the variability of inferred likelihood ratios of <3%.

Eq. (2) may only be formally solved by first assuming a specific number of contributors for mixed samples, and the same authors in reference [2] point out that this requirement is a deficiency of their approach. Currently, the number of contributors must be first inferred by the analyst and provided as input, or determined algorithmically using several recently communicated methods. The number of contributors to a DNA profile cannot be known with certainty. Assignment of this number, especially when including a low copy minor contributor with allelic content comparable to stutter noise, is a particular challenge. These cases could falsely introduce an additional contributor to a genotype set, with the potential to generate an $LR_c$ value favoring inclusion of non-contributors. Conversely, underestimating the number of contributors could yield $LR_c$ values favoring the exclusion of a true contributor. Both potential outcomes are problematic. A formal technical approach enabling computation of $LR_c$ values when the number of contributors is unknown and that further allows the contributor number to be inferenced based on the weight of the evidence for and against a particular value, would be highly desirable. The ability to provide a generalization of Eq. (2) incorporating model goodness-of-fit weightings $w_j$ derived from models of arbitrary model order (numbers of contributors), thereby obtaining $LR_c$ with the minimum a priori assumptions would be particularly desirable.

Information Theory, Model Selection, and Akaike Weights

The fundamental problem to be addresses is that for any process with measurement noise, the likelihood of the data given a model, Pr $(G_c|S_j)$ in Eq. (1), when the model's adjustable parameters are estimated from fitting to the data, will increase as the number of parameters increases (e.g., the number of contributors). One can surmise that when the number of adjustable parameter exceeds a threshold number, a fitted model will begin to reproduce features of the specific realization of the noise in the one instantiation of the evidentiary data set in addition to the features of the underlying generative process of interest. This phenomenon is generally termed "over-fitting". The assignment of low-level PCR stutter noise peaks in a DNA profile to an additional sample contributor is an example of over-fitting.

The concept of parsimony is important in the selection of which model is "best" for making inferences from a data set. Parsimony is the concept that a model should be as simple as possible concerning the included variables, model structure, and number of parameters. Parsimony is a desired characteristic of a model used for inference, and it is usually defined through a trade-off between squared bias and the variance of parameter estimators. Parsimony trades off between the evils of under- and over-fitting of data to a model. Another important concept is that the underlying true model of a process is not knowable and is assumed to be of infinite dimensions. This is particularly true in the forensic DNA context where not only the number of contributors is unknown, but thermodynamics, the presence of unknowable background amplification inhibitors, can produce biases in DNA amplification across loci, across specific alleles within loci, and introduce variable stutter noise for different alleles. Template switching during PCR may introduce spurious allelic content. Further, polymerases can introduce PCR incorporation errors that can confound mixture interpretation. Finally, there are variations in the measurement system itself, such a run-specific nonlinearities in signal intensity with concentration and other factors. The STRMix software attempts to integrate over many of these nuisance parameters, which is one approach to representing the unknown and unknowable model responsible for the observed data G produced by an end-to-end analysis of a given DNA specimen.

A useful framework for model selection (the models structure and number of adjustable parameters to include) was derived by Akaike and is based on the information theoretical concept of minimum information loss. Akaike's [5] seminal paper proposed the use of the concepts of "distance between models", as embodied through a specific representation of distance called the Kullback-Leibler information (K-L distance), as a fundamental basis for model selection. The K-L information, I(f, g), between two models, f and g, is defined through a specific integral, and it is similar to others descriptions of information between models, such as the Boltzmann information [6]. Its specific form is beyond the scope of our discussion here, but it describes the "information lost when a model g is used to approximate f". In the present context, f is the unknowable "true" model of the data generation process, and g is the model desired to estimate to perform inferences from the data. The Akaike model selection criterion is a formal approach to choose the model g that will minimize the expected information lost when g is used to approximate f. While f is not known, Akaike found a rigorous method to estimate the expected K-L information loss based on the empirical maximum log-likelihood of the data. His criterion permits ranking (assigning of relative probabilities or relative weights) to different models, based on the concept of information lost with respect to the unknown true model, regardless of the fact that models may have different numbers of adjustable parameters. For present purposes, the criterion will enable an analyst to weight different mixture DNA models with different numbers of contributors and to then inference parameter values, such as contributor proportions and the number of contributors based on the weight of the evidence using the minimum of assumptions.

Akaike's information criterion is defined as [4]:

$$AIC = 2 \ln(L(\hat{\theta})) + 2K, \qquad \text{Eq. (3)}$$

where L is the likelihood function, $\theta$, is the vector of adjustable parameters, and K is the number of adjustable parameters estimated in the fitting [3]. The quantity $L(\hat{\theta})$ in Eq. (3) is the value of the likelihood function at its maximum value, which we obtain through a fitting procedures that adjusts the values of the K parameters to achieve the maximized L. The importance of the AIC in addressing the "over-fitting" problem is evident from the signs of the two terms in Eq. (3). Information loss I(f, g) is always made smaller when adding more specific known parameters in an approximating model g, however, when these parameters are not known, and must be estimated from the data (rather than being known), further uncertainty is added to the estimation of the information loss I(f, g). At some number of additional parameters the net information loss will increase, rather than decrease, due to "noisiness" in the unknown values of the adjustable parameters that are not really needed to achieve an acceptable model. The first term on the right hand side of Eq. (3) tends to decrease as more parameters are added (the likelihood of the data given the model increases), while the second terms, 2K, gets larger as more parameters are added to the model. The AIC, implements the trade-off between and under-fitting and over-fitting that is the principle of parsimony. The AIC penalizes for the addition of parameters, and thus selects the model that fits well, but has a minimum number of parameters.

The result in Eq. (3) is asymptotic (large number of data points in the fitting). For small numbers of fitted data points $n_P$ ($n_P/K<\sim40$), the use of a corrected AIC value, AICc, the second-order Akaike criterion derived by Suguira, is recommended [5]:

$$AIC_c = AIC + \frac{2K(K+1)}{n_P - K - 1} \qquad \text{Eq. (4)}$$

Note that Eq. (4) reduces to Eq. (3) with $n_P$ is large with respect to K, i.e., the number of fitted data points greatly exceeds the number of parameters to be estimated.

To compute AIC values, it remains for us to define the likelihood function appropriate for our modeling problem. As these methods will ultimately be applied to next generation DNA sequencing data (according to certain embodiments), rather than electropherograms (although the methodology applies equally well in this case), some simplifying assumptions are adopted for present purposes. In particular, we can assume a simple measurement noise model, whereby allelic data fluctuates according to counting statistics that are approximated as Gaussian statistics for sufficiently large read counts. We are presently characterizing statistics for measurement in next generation sequencing systems. For electropherogram data, these fluctuations are estimated to be log normal, with the standard deviation varying with the expected peak height. As measurement models are made available for next generation sequencing of forensic loci, through our further research and publications of others, we will incorporate these models into our framework. We adopt the notation of reference [1] and represent the evidence G as the measured allelic proportion a for locus l using the variable $O_{l,a}$. Likewise, for the generative model, g, that we seek to fit to the data, we represent through a vector, E, the model predicted expected allelic proportion for allele a at locus l. We can now write the likelihood function for the genotype set j as:

$$L_j(\theta \mid O) = \prod_{l=1}^{Loci} \prod_{a=1}^{A(l)} \frac{1}{\sqrt{2\pi}\sigma_a} e^{-\frac{(E_{l,a}^j(\theta) - O_{l,a})^2}{2\sigma_a^2}}, \qquad \text{Eq. (5)}$$

where the product is over all alleles A for each locus and over all loci, and the parameter θ is the vector of the K independent parameter values to be fit to the data. Without loss of generality, we introduce the simplifying assumption that the uncertainties $\sigma_a$ are a fixed value σ independent of allelic proportion, and obtain the following expression for $\ln(L_j(\theta|O))$ that we must maximize over θ to compute the AIC for model g for genotype set j:

$$\ln(L_j(\theta \mid O)) = -\frac{n_P}{2}\ln(2\pi\sigma) - \frac{1}{2\sigma^2}\sum_{l=1}^{Loci}\sum_{a=1}^{a(l)} \frac{(E_{l,a}^j(\theta) - O_{l,a})^2}{2\sigma^2}, \qquad \text{Eq. (6)}$$

where $n_P$, the number of data points is given by $$n_P = \sum_{l=1}^{Loci} a(l).$$

For each genotype set j the model g presumes a specific number, n, of contributors (that varies across the set of models for g) producing the predicted allelic data E. The AIC value is computed with K=n−1, since we constrain the proportion set θ for the contributors to sum to 1.0 (giving one fewer degree of freedom). We compute the AIC for a complete set of R models, one for each genotype set j, with each evaluated its maximum likelihood parameter values $\hat{\theta}$.

Two measures associated with the AIC values for a set of candidate models can be used to compare models, the delta AIC, and Akaike weights. The delta AIC, $\Delta_i$, is a measure of the strength of model i in the set R [3]:

$$\Delta_i = AIC_i - AIC_{min}, \qquad \text{Eq. (7)}$$

where the quantity $AIC_{min}$ is the AIC value of the best model among the complete set of R models. The $\Delta_i$ estimate the relative expected K-L distances between the unknown "true" model f and the model $g_i$ in the set of R models. The $\Delta_i$ are easy to interpret and allow a quick comparison and ranking of models. The model estimated to be the "best" has $\Delta_i \equiv \Delta_{min} \equiv 0$. The larger the $\Delta_i$ is, the less plausible it is that the fitted model is the K-L best model.

Returning to the task of computing the Likelihood Ratios using re-derived weightings in Eq. (2) based on information theoretic considerations, we use Akaike's quantitative expression for the likelihood of a model, $g_i$, given the data, for each model in the set. Akaike showed [8] that this likelihood is proportional to $\exp(-\Delta_i/2)$ [6]. The likelihood of a model being the best model is given by an Akaike weight, $w_i^*$, expressed as:

$$w_i^* = \frac{e^{-\Delta_i/2}}{\sum_{k=1}^{R} e^{-\Delta_k/2}}. \qquad \text{Eq. (8)}$$

The $w_i^*$ is the weight of evidence in favor of model $g_i$ being the actual best model given the data. This interpretation is consistent with the weightings applied in Eq. (2), and we will use these weights in the calculation of Likelihood Ratios and other quantities of interest. As a final note, we point out that the model weights reflect the relative likelihoods among the chosen set of R models. It is incumbent upon the analyst to choose a model structure that most accurately represents the underlying generative and measurement process. As the procedure to determine the model weights computes the maximum likelihood fit for each model, we can additionally quantify whether the best model among the set R achieves an acceptable "goodness-of-fit", for example, using the chi-squared test with degrees of freedom given by the number of fitted data points minus the number of fit parameters K. We anticipate that when unacceptable chi-squared values are obtained, the set of model orders considered may be too low to represent the data, and this statistic will inform us when this is the case. As a practical implementation issue, the number of genotype sets J(n), for a model order (contributors) n, become explosively large with increasing n, and pruning J so that the estimation of $w_i^*$ is computationally tractable is a technical implementation challenge that currently limits consideration to model orders of $n_{max} \sim 4$ persons or fewer on desktop computers.

Computation of the Quantities of Interest Using Akaike Weights

We can now define a generalized $LR_c$, which we will label $LR_c^*$ that computes the desired likelihood ratio for the POI under $H_1$ and $H_2$ without the a priori assignment of a specific number of contributors:

$$LR_c^* = \frac{\sum_{i=1}^{n_{max}} \sum_{j=1}^{J(i)} w_j^* Pr(S_j | H_1)}{\sum_{i=1}^{N_{max}} \sum_{j=1}^{J'(i)} w_{j'}^* Pr(S_{j'} | H_2)},$$ Eq. (9)

where the second sum now runs over all model orders and the genotypes sets run over all of the J pertinent genotype sets for each model order to be considered in the analysis. As in reference [1], we also consider evaluation of Eq. (9) that does not require us to take the two competing hypothesis into account. In this case, we are assessing the evidentiary weight that a genotype is present in the sample given the data. We will call this quantity the Evidence Ratio for the genotype, $ER_G$, which can be computed as follows:

$$ER_G = \frac{\sum_{i=1}^{n_{max}} \sum_{m=1}^{r(i)} w_m^*}{\sum_{i=1}^{n_{max}} \sum_{m'=1}^{r'(i)} w_{m'}^*}.$$ Eq. (10)

Here, the outer sum runs over all model orders that are considered, and the inner sum in the numerator of Eq. (10) is the subset, r, of the R models for each respective model order that contains the genotype of interest, while that in the denominator is for all models that do not contain the genotype of interest. We give an example of the application of Eq. (10) to a 3-person mixture of CODIS autosomal STRs in the next section.

Finally, we can write a similar expression to Eq. (10) to provide and evidence ratio $ER_c^n$ to inference the number of contributors based on Akaike weights of all models in the set:

$$ER_c^n = \frac{\sum_{m=1}^{r(n)} w_m^*}{\sum_{i \neq 1}^{n_{max}} \sum_{m'=1}^{r(i)} w_{m'}^*},$$ Eq. (11)

where r(n) is the subset of the R models with n contributors, and the denominator is the sum of all Akaike weights for the subset of models that do not contain n contributors. In this way, the actual number of contributors is inferenced based on the weight of the evidence, rather than specified a priori.

Application to Database Searching with Mixed Contributor DNA Profiles

To illustrate the application of the tools derived in the previous section, we apply them to the problem of searching a database to test for a matching genotype given a sample containing multiple contributors. A similar analysis was performed in Reference [2] for the STRMix algorithm. Here, rather than focus on the Likelihood Ratio $LR_c^*$, we apply Eq. (10) to compute the Evidence Ratio $ER_G$ for the contributor genotypes and the non-contributor genotypes in a population database given simulated evidence. To perform the analysis, we used a database of human genotypes compiled and published by NIST that contains >1000 genotypes encompassing all major ethnic groups. Genotypes for the 13 standard CODIS loci were extracted and used for the analysis.

Figure 2:
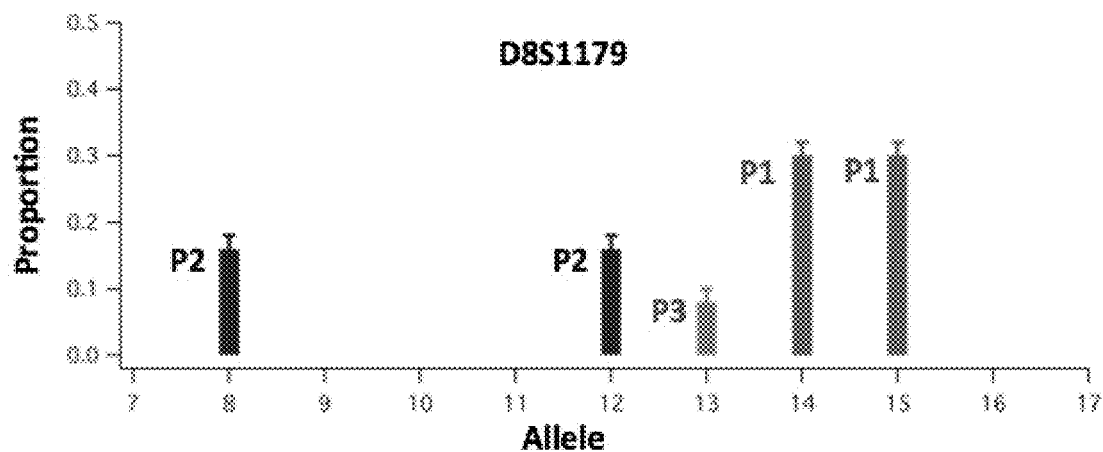
FIG. 2 illustrates an example of simulated allelic profile for a 3-person mixture with no allelic overlap.

We performed 10 simulated experiments in which 3 persons were chosen at random from the NIST database. The proportions for the three contributors, which we call P1, P2, and P3, were set to the values 0.6, 0.32, and 0.08, respectively. Allelic profiles for each locus were constructed based on the contributor proportions and overlapping alleles. The allelic peak heights of the profile were randomly perturbed according to a Gaussian distribution with standard deviation $\sigma$ of 0.02. An example simulated profile for locus D8S1179 is shown in FIG. 2. Persons P1 (14, 15) and P2 (8, 12) where heterozygous, whereas the lowest proportion contributor, P3, was homozygous (13,13). For the illustrative purposes of this analysis, we did not include stutter peaks in the simulation model for the profile, or in generative model for the model set g, for which we will compute the Akaike weights $w_i^*$. We have also restricted the model order for g to be n=3. For a 3-person model of an autosomal locus, there are R=1771 genotype sets J, following pruning for duplication, for which we need to compute AIC values to obtain the weights. To compute the AIC, we maximize $\ln(L_1(\theta|O))$ in Eq. (6) over possible assignments of the three proportion values ($\theta$) to obtain a maximum likelihood value LA. $AIC_c$ values for K=2 are then computed using Eq. (4), $\Delta_i$, values are computed using Eq. (7), and then weights $w_i^*$ are computed using Eq. (8). For each of the 3 contributing genotypes, we then perform the respective sums in Eq. (10), where the weights for models containing the genotype are used in the numerator, and those for models that do not contain the contributor genotypes are used in the denominator. The resulting Evidence Ratio $ER_G$ gives the weight of evidence in favor of the presence of the queried genotype in the sample over the weight of evidence against the presence of the genotype. A value of $ER_G$=1.0 is obtained for the fully ambiguous case. The result of this analysis for the D8S1179 allelic data shown in FIG. 2 is shown in the table below:

| Locus D8S1179 | | | |
| --- | --- | --- | --- |
| Person | Genotype | Proportion | $ER_G$ |
| P1 | 14, 15 | 0.6 | 3865.3 |
| P2 | 8, 12 | 0.32 | 1429.2 |
| P3 | 13, 13 | 0.08 | 27.0 |

Figure 3:
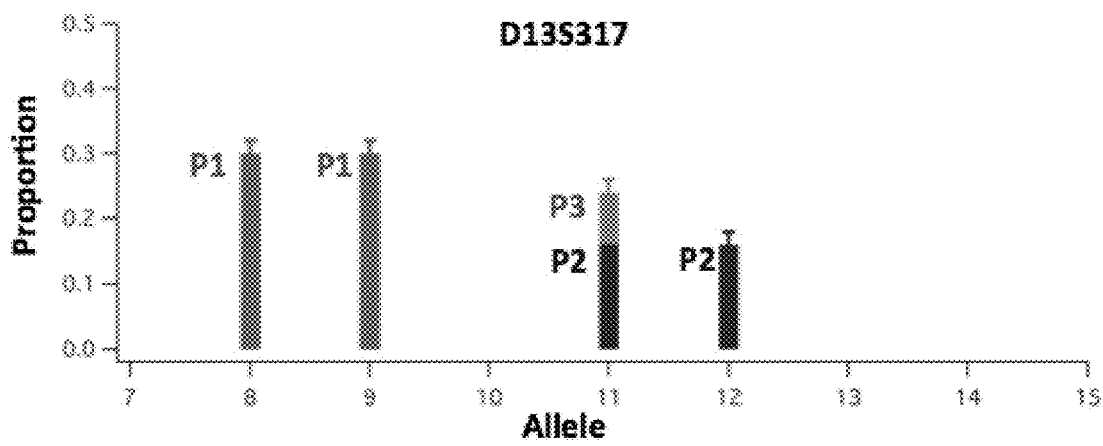
FIG. 3 illustrates an example of simulated allelic profile for a 3-person mixture with significant allelic overlap.

The high value of $ER_G \gg 1.0$ indicates strong evidence in favor of the presence of the true contributing genotypes at this locus. A specific threshold value of $ER_G$ for "calling" the genotype detected will depend on the tolerance for false, non-contributor genotype detections that will be tolerable by the analyst given the circumstances. We provide a method to determine a suitable threshold based on a specific population database below. The importance of this "false alarm" analysis is clearly illustrated by our second example, which shows D13S17 locus data in FIG. 3.

Here persons P1 and P2 are heterozygous, but P3 is homozygous and shares an allele 11 with P2. As in FIG. 2, we include the error bar, which indicates one standard deviation of the simulated measurement noise. It is immediately apparent that given this noise, there is significant potential ambiguity in the data regarding the presence or absence of a false chimeric genotype such as (9, 11), which was not a contributing genotype to the sample. This uncertainty is reflected in the $ER_G$ values we obtained for the contributing genotypes in this locus:

| Locus D13S317 | | | |
|---|---|---|---|
| Person | Genotype | Proportion | $ER_G$ |
| P1 | 8, 9 | 0.6 | 5.5 |
| P2 | 11, 12 | 0.32 | 0.8 |
| P3 | 11, 11 | 0.08 | 0.1 |

In this case, the only contributor genotype in which the weight of the evidence exceeded 1.0 based on the $ER_G$ is for P1, the major contributor. The reduced $ER_G$ for P1 compared to those in the table for Locus D8S1179 is reflective of the fact that other potential assignments to the pairing of the detected alleles for P1 have considerable support in the data and this is reflected in the low $ER_G$ value. For P2, and P3, the Akaike weights (i.e., "goodness-of-fit" corrected for number of fit parameters) for genotype sets without the contributor on average outweighed those with the contributor. In such cases, it is likely non-contributing genotypes in a database could produce $ER_G$ values that exceed those of the minor actual contributor types for these data, thereby producing false detections.

Figure 4:
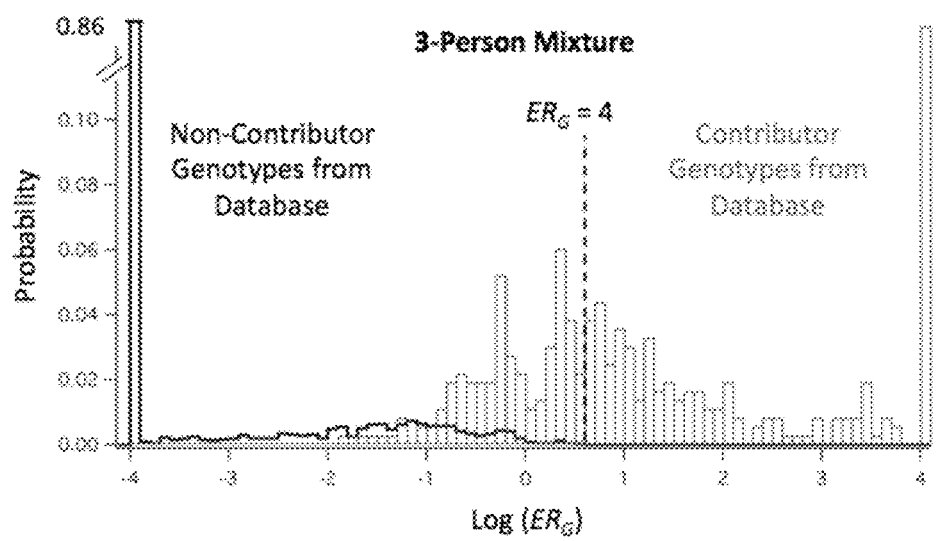
FIG. 4 illustrates a distribution of Evidence Ratio, $ER_G$, values for contributor and non-contributor genotypes over the set of all forensic genetic loci used in the CODIS FBI loci set for contributor proportions P1, P2, P3 and genotypes for the P1, P2, P3 chosen at random from a database of human forensic genotypes.

To estimate the false detection rates and distribution of non-contributor genotype the $ER_G$ values, we first removed the 3 contributors from the database for each of the 10 simulated experiments and then identified all unique non-contributor genotypes in the database for each locus. The identical analysis as above was then performed for genotypes over all loci for the unique non-contributor genotypes. The results are shown in FIG. 4. Here, for visualization purposes, we have collapsed all $ER_G$ values >10,000 to the value 10,000 and all $ER_G$ value <0.0001 to 0.0001.

Figure 5:
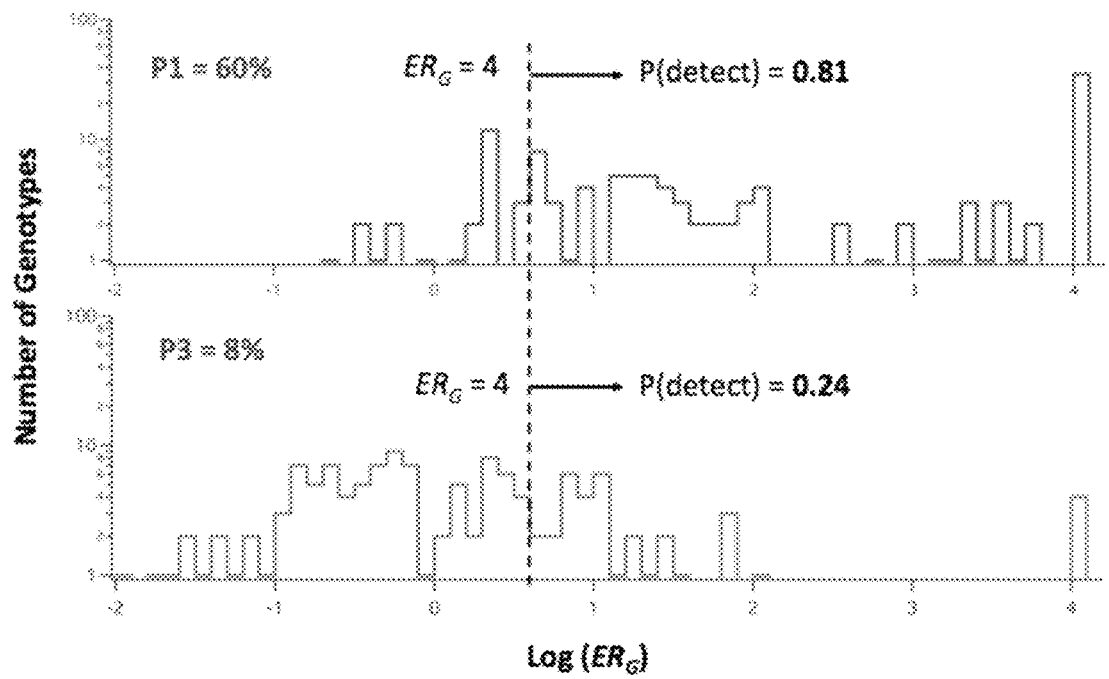
FIG. 5 illustrates a breakout of the contributor $ER_G$ value genotype distribution from FIG. 3 into P1 and P3 genotypes, in which given a detection threshold value of 4, there is a greater than 3 times a high chance of detecting the major contributor versus the smaller minor contributor in the 3-person mixture.

There is significant overlap of the distributions toward the tail end of the non-contributor genotype distribution. The highest $ER_G$ value obtained for a non-contributor was ~4.0, or Log($ER_G$)~0.6, which is shown by the dotted line in the figure. The fraction of contributor genotypes exceeding thus threshold value of 4 is 0.6. We note that the distribution used to derived the threshold is depends on the order of the simulated mixture sample, the specific contributor proportions in that sample, and the genotypes in the specific population database. It does however give a general idea of the trade-off between probability of detecting a contributor genotype and getting a false detection from a non-contributor arising from factors such as the magnitude of the measurement noise, allelic overlap of the contributors in the mixture, and population genotype diversity at the forensic loci of interest. Importantly, if we break down the distribution of $ER_G$ values from contributor genotypes into those for P1 versus P2, we obtain the intuitive result shown in FIG. 5.

Here the portion of the distribution in FIG. 4 attributed to the major contributor P1 is highly biased toward the higher $ER_G$ values compared to the smaller minor contributor. The detection rate is >3 fold higher for the major contributor for the threshold value of 4.0.

Figure 6:
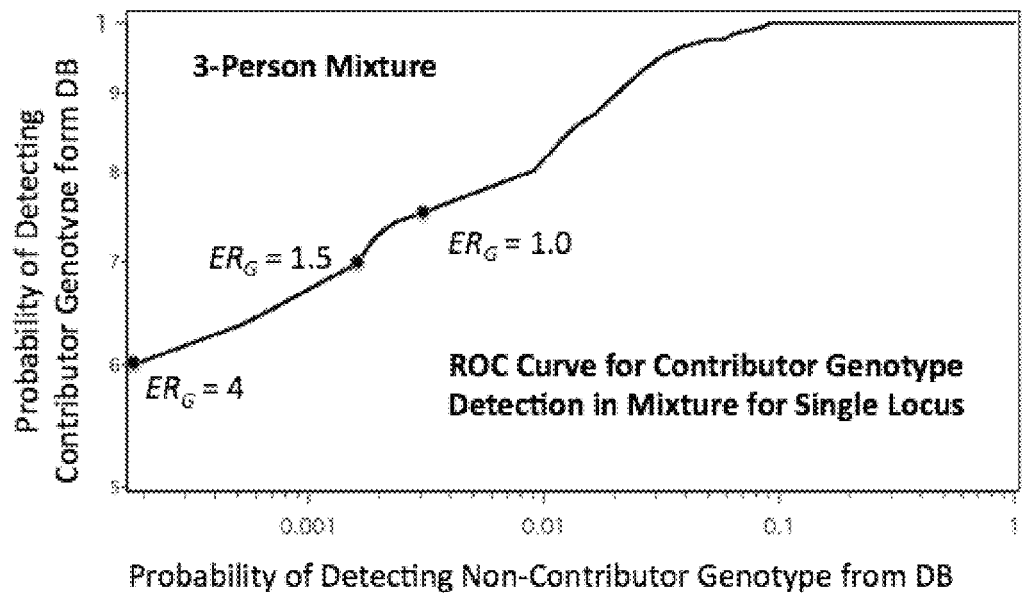
FIG. 6 illustrates a Receiver Operating Characteristic (ROC) curve derived from the distribution shown in FIG. 4, which depicts the tradeoff between the probability of detecting a contributor genotype and probability of falsely detecting a non-contributor genotype from the database of genotypes; wherein each choice of threshold value produces a point on the curve.

While specific threshold values may be chosen depending on the context of the analysis, the general description of the algorithmic performance is captured by a receiver operating characteristic (ROC) curve where the results from the set of thresholds are summarized. In this representation the threshold value is varied and detected fraction of true positives and false positives for each threshold is computed and plotted as a parametric curve. We have plotted the ROC curve in FIG. 6 for the distributions shown in FIG. 4. To contextualize this result, let us choose the threshold value for detecting a contributor genotype and read off the false alarm rate. We can then use these values to estimate the performance of the system when querying a database of a specific size. As an example, if we choose the threshold value of $ER_G$=4, the probability that a non-contributor genotype will exceed this value by chance when score against a 3-person mixtures sample with P1, P2, and P3 at the proportions specified above is ~0.00012 per locus. The probability of detecting a contributor genotype is ~0.6 averaged. If we type the 13 CODIS loci for this mixture, then the expected number of contributor genotypes we will detect for a POI with known genotype will be ~8 loci (an 8 locus profile). The probability that this profile will contain an accidental match of the genotype from the non-contributor database at 1 or more of the 8 loci is given by $1-(1-0.00012)^8$ or ~1/1,000 chance. To use this 8-locus match in casework, we would need to add the criterion that the queried genotype is not excluded at the remaining 5 loci. Note for the analysis above, we used the average locus distribution. This calculation could be readily generalized to include locus-specific non-contributor match probabilities. A similar calculation applies where each entry in the genotype database is queried for genotypes matches. For a 1/1,000 chance of a calling an 8 locus detection falsely, a database of 1,000 people will on average produce one false 8 locus hit, a database of 10,000 people will produce 10 false matches at 8 loci, etc. Fortunately, as next generation DNA sequencing will undoubtedly proliferate the number of unique alleles (using whole sequences for each locus), the potential for false matches in database searching using multi-contributor profiles may be significantly reduced.

Although most of the exemplary embodiments discussed herein have been provided within the context of mixed contributor forensic samples, certain embodiments of the present invention can be equally applicable and revolutionary in microbial and plant forensics analysis through the ability to provide high accuracy deconvolution of complex mixed samples.

Working Example

Figure 8:
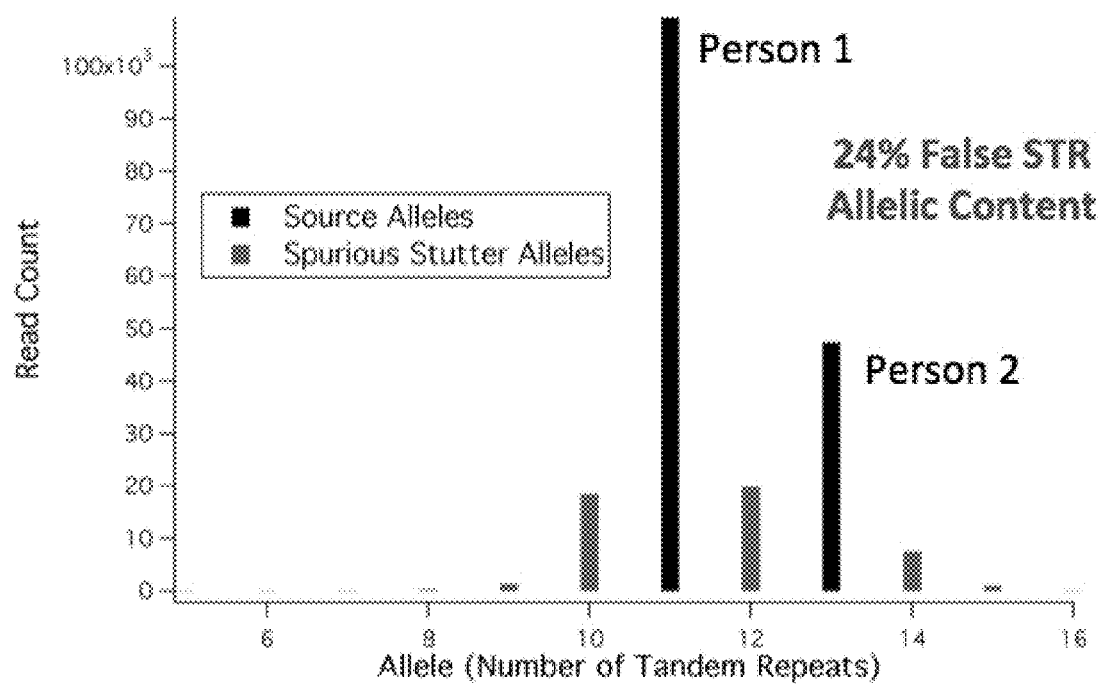
FIG. 8 shows the true alleles and spurious alleles detected from analysis of the 2 person samples without the application of the error-free single molecule sequencing method according to certain embodiments of the present invention.
Figure 9:
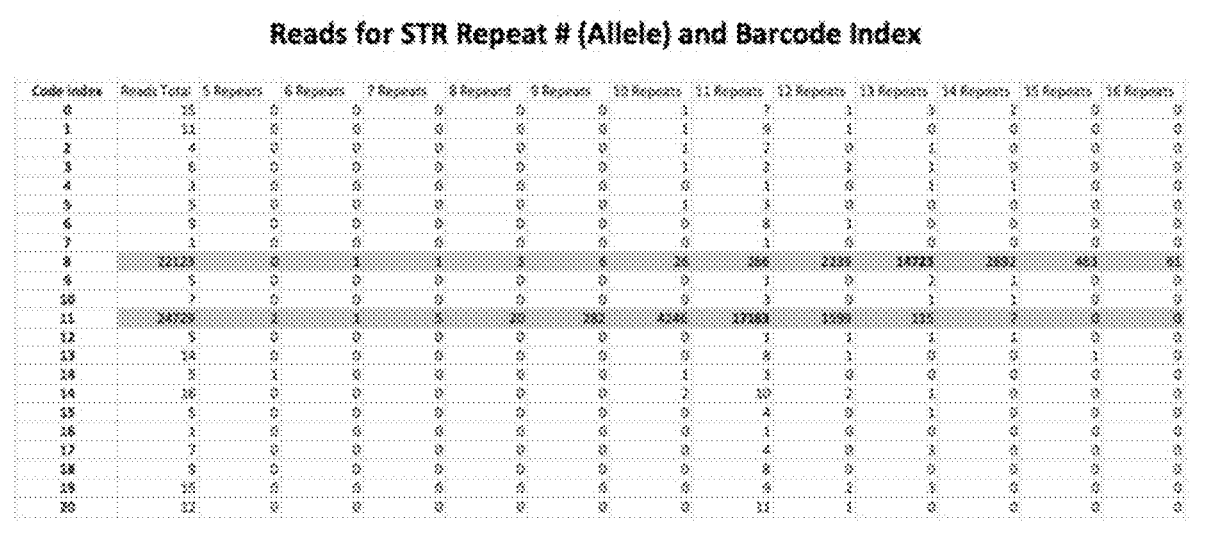
Figure 10:
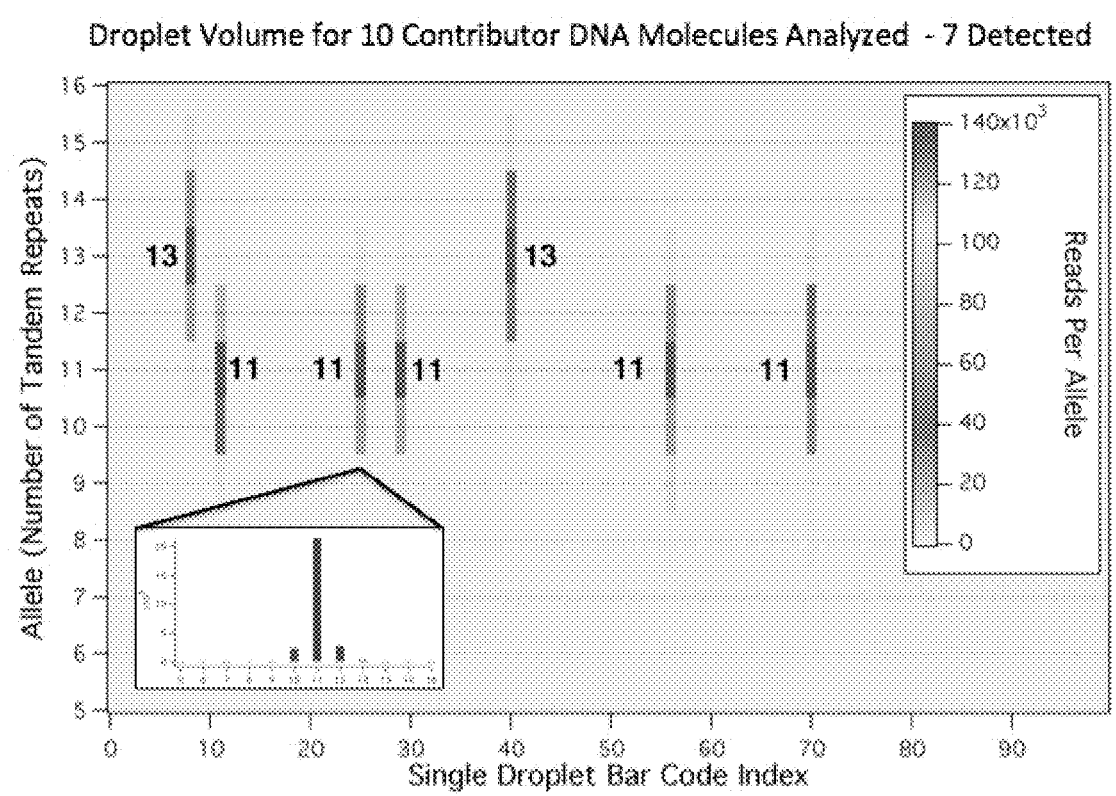
FIG. 10 shows similar data to FIG. 9 but for all 100 barcoded primers used for the proof-of-concept experiment.
Figure 11:
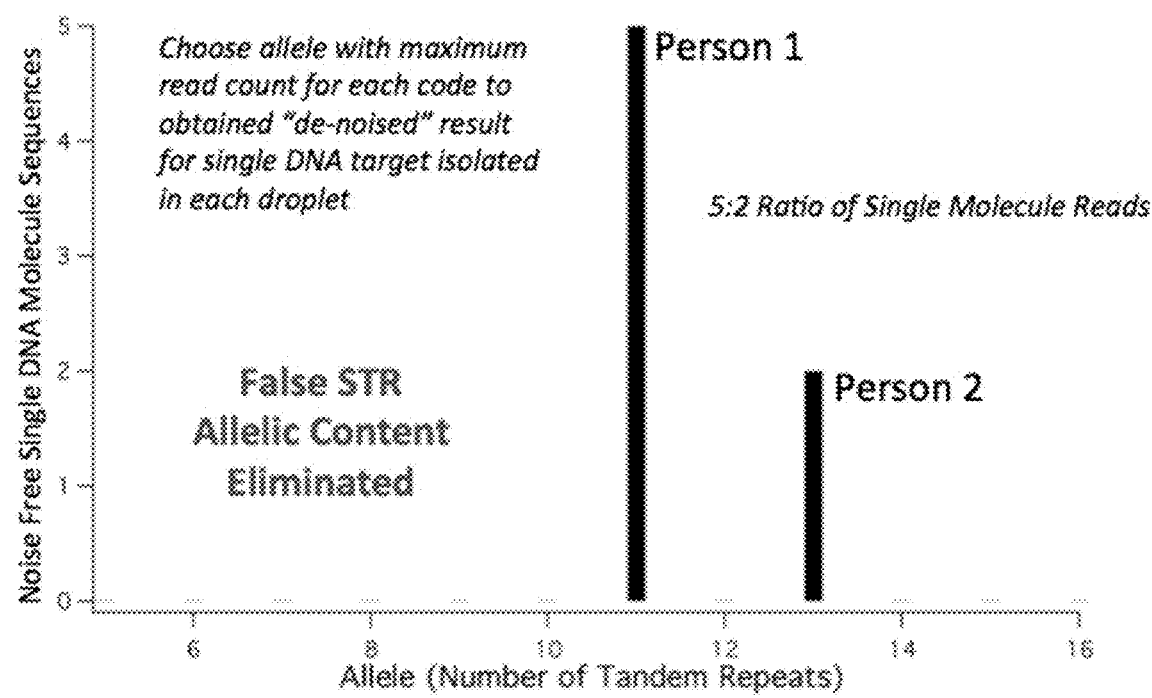
FIG. 11 shows the data from FIG. 10 following bioinformatics analysis to collapse all read data for each barcode to yield error-free, single molecule sequences, and perfect resolving of the mixture samples of 2 males.

The present disclosure is further illustrated by the following example, which in no way should be construed as being limiting. That is, the specific features described in the following examples are merely illustrative, and not limiting In FIG. 7, we show a specific representative example mixture case that we wish to deconvolve and list the specific noise sources the methodology we apply will eliminate. A complete end-to-end analysis, similar to that depicted in FIG. 1 was applied to a sample with a mixture of 2 males and the amplification and sequencing analysis performed for a specific STR forensic locus, DYS392, with the males mixed in a ratio of 2:1, with alleles 11 and 13, as the major and minor contributor, respectively. FIG. 8 shows the results of sequencing analysis in the absence of collapsing all sequencer reads to their respective barcodes. As shown in red, the is approximately 24% spurious content introduced into the sample due to PCR stutter, and the sample, as processed, could be interpreted as containing anywhere from 2-8 contributors, all at different proportions of total DNA. Following informatic analysis, whereby, all sequencer reads for the amplicons are collected by barcodes, we obtain the data shown in FIG. 9. The volume equivalent of 10 target DNA molecules was collected for the analysis and 100 unique primer barcodes were used. The allelic content for the first 20 barcodes is indicated in the table. For each barcode, the stutter pattern is evident, but a clear, dominant allele is also evident, and this represents the allele of the single encapsulated target associated with that barcode. A summary of the data over all 100 barcodes is shown in FIG. 10. As we anticipated collecting an average of 10 target molecules, we do not expect to collect exactly 10 in any given experiment. In this case, we collected 7 targets. FIG. 11 depicts the new allelic profile of the mixture following our single molecule methodology, and it is now completely "de-noised", there is no spurious content. Further the ratio of now "error-free" molecule reads is 5:2, in concordance with the input DNA mixture ratio. The deviation is due to the Poisson sampling (counting) statistics.

Figure 12:
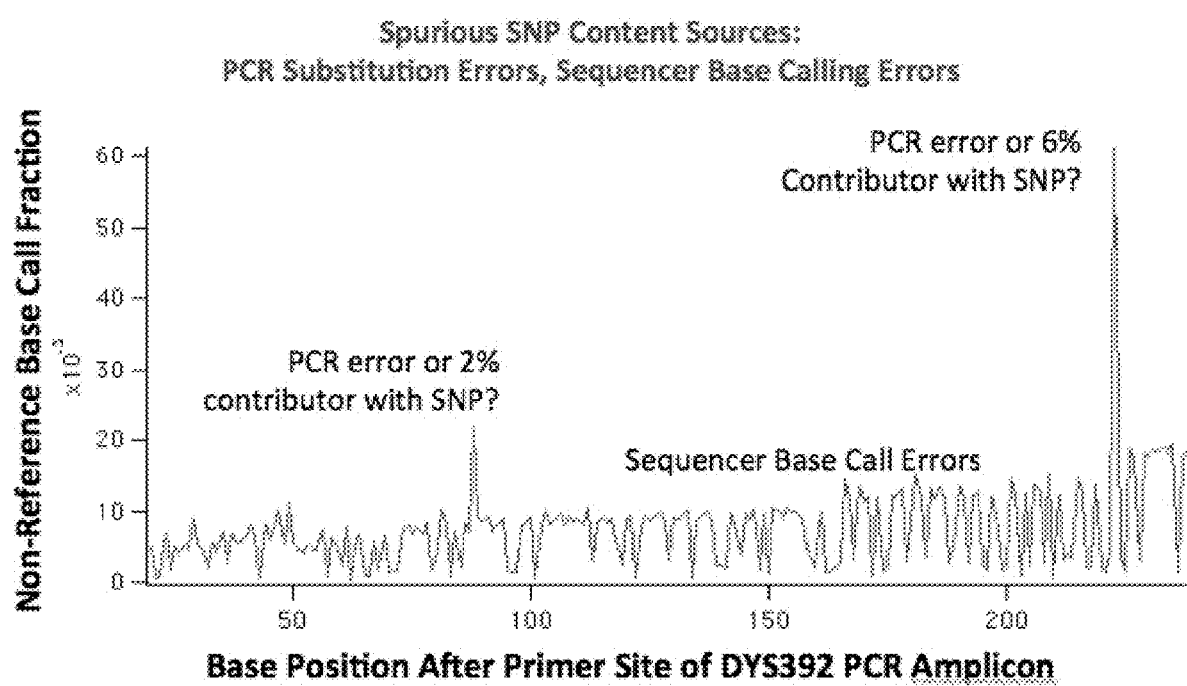
FIG. 12 shows the distribution of non-reference base calls over the Y-chromosome PCR amplicon away from the short tandem repeat region without application of the error-free method according to certain embodiments of the present invention, indicating the sources of spurious single nucleotide polymorphism-like content due to amplification artifacts and sequencer base calling errors.
Figure 13:
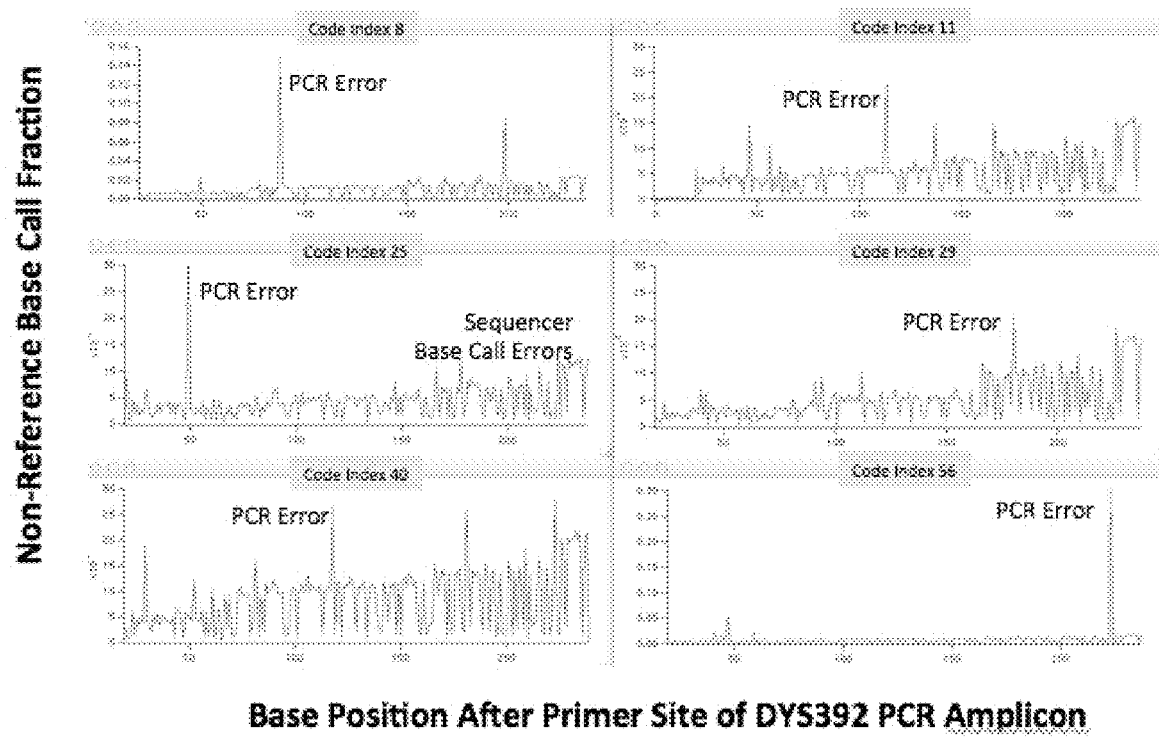
FIG. 13 shows the data from FIG. 12 broken out by barcode value. Application of an informatics algorithm that chooses the base call >50% of the total for each base position will remove all spurious content and yield and error-free sequence for this region of the amplicon for each barcode.

We now examine in the representative example, the non-STR portion of the Y-locus DYS392. With the advent of NGS, STR data will be supplemented by the presence of SNPs that can increase the specificity of an allele a given locus for a given individual. In FIG. 12, we show the fraction of non-reference base calls at each base position over all reads in the analysis. The lower baseline miscalled bases are due to NGS base calling errors, while the spikes are due to PCR errors that occurred during early cycles during thermal cycling an amplified to a proportion that is statistically significant with respect to the baseline base calling error rate. In the absence of our barcoding method, this false content mimics 2% or 6% potential contributors with shared STR allelic sections, but variable SNPs in other regions of the amplicon. FIG. 8 shows the distributions shown in FIG. 13, but not broken down by individual barcode. It is clear that are varying PCR error sites for each barcode, and that none are more than 50% of the total reads. Thus, our algorithm, that selects the majority base call for each base position will yield a noise free sequence for the single molecule target associated with each code.

These and other modifications and variations to the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

Figure 14:
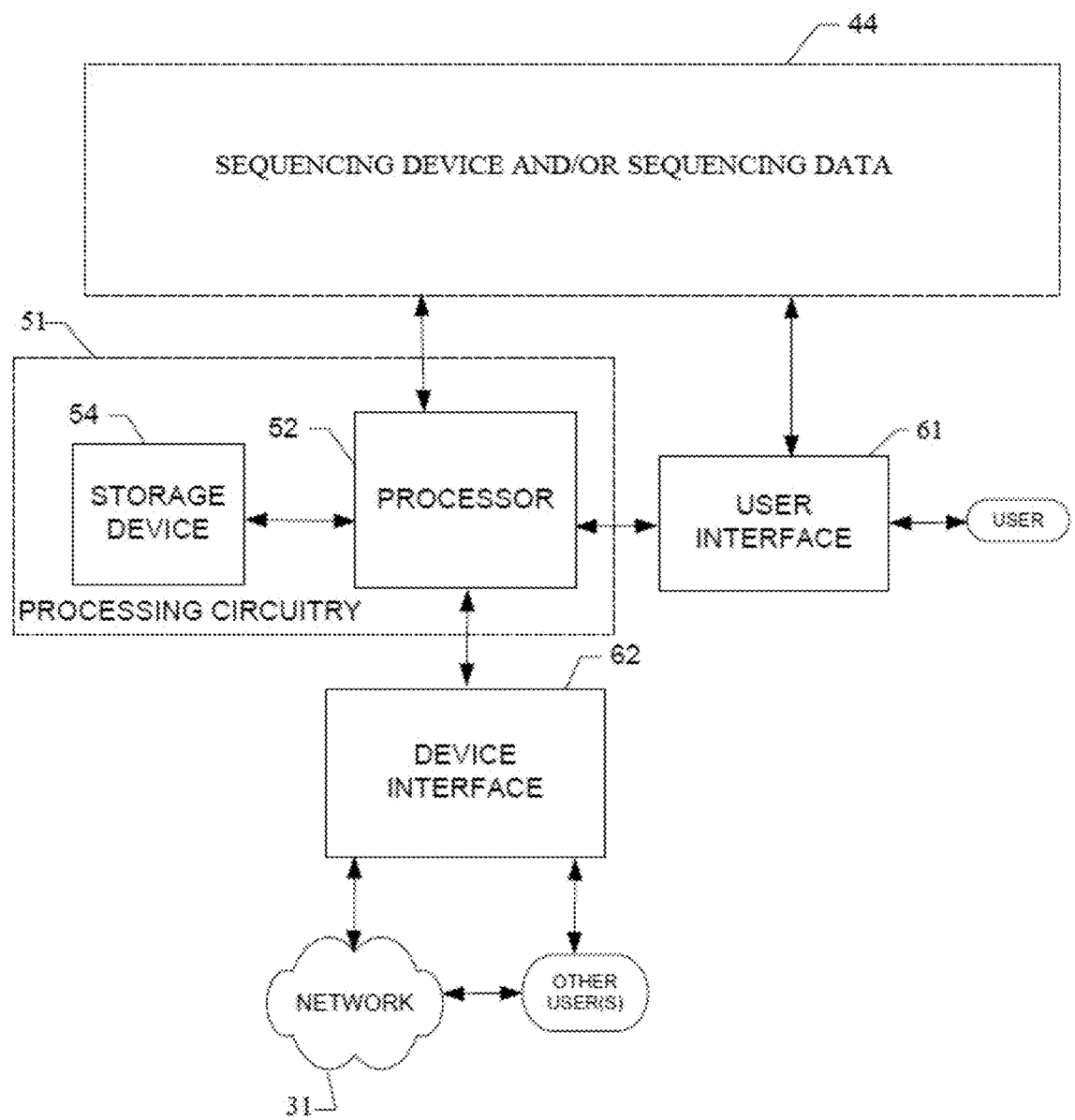
FIG. 14 illustrates a functional block diagram of an apparatus that may be useful in connection with certain embodiments of the present invention.

Referring now to FIG. 14, an apparatus or system for provision of performing an Evidence Ratio test or the like as discussed throughout the specification above, for example, in accordance with an example embodiment is provided. In an example embodiment, the apparatus may include or otherwise be in communication with processing circuitry 51 that is configured to perform data processing, application execution and other processing and management services according to an example embodiment of the present invention. In one embodiment, the processing circuitry 51 may include a storage device 54 and a processor 52 that may be in communication with or otherwise control a user interface 61 (which may be optional) and a device interface 62. As such, the processing circuitry 51 may be embodied as a circuit chip (e.g., an integrated circuit chip) configured (e.g., with hardware, software or a combination of hardware and software) to perform operations described herein. However, in some embodiments, the processing circuitry 51 may be embodied as a portion of a server, computer, laptop, workstation or even one of various mobile computing devices. In situations where the processing circuitry 51 is embodied as a server or at a remotely located computing device, the user interface 61 (if employed at all) may be disposed at another device (e.g., at a computer terminal or client device) that may be in communication with the processing circuitry 51 via the device interface 62 and/or a network (e.g., network 31).

The user interface 61 (if employed) may be in communication with the processing circuitry 51 to receive an indication of a user input at the user interface 61 and/or to provide an audible, visual, mechanical or other output to the user. As such, the user interface 61 may include, for example, a keyboard, a mouse, a joystick, a display, a touch screen, a microphone, a speaker, a cell phone, or other input/output mechanisms. In embodiments where the apparatus is embodied at a server or other network entity, the user interface 61 may be limited or even eliminated in some cases. Alternatively, as indicated above, the user interface 61 may be remotely located.

The device interface 62 may include one or more interface mechanisms for enabling communication with other devices and/or networks. In some cases, the device interface 62 may be any means such as a device or circuitry embodied in either hardware, software, or a combination of hardware and software that is configured to receive and/or transmit data from/to a network and/or any other device or module in communication with the processing circuitry 51. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an example embodiment, the storage device 54 may include one or more non-transitory storage or memory devices such as, for example, volatile and/or non-volatile memory that may be either fixed or removable. The storage device 54 may be configured to store information, data, applications, instructions or the like for enabling the apparatus to carry out various functions in accordance with certain embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases that may store a variety of files, contents or data sets. Among the contents of the storage device 54, applications may be stored for execution by the processor 52 in order to carry out the functionality associated with each respective application (e.g., analysis of DNA sequencing data including an Evidence Ratio test).

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an example embodiment, the processor 52 (or the processing circuitry 51) may be embodied as, include or otherwise control the sequencing device, related circuitry, or related data 44, which may be any means such as a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the sequencing device, related circuitry, or related data 44 as described herein.

REFERENCES

[1] D. Taylor, J. Bright, J. Buckleton, The interpretation of single source and mixed DNA profiles, Forensic Science International: Genetics, 7 (2013) 516-528.

[2] J. Bright, D. Taylor, J. Curran, J. Buckleton, Searching mixed DNA profiles directly against profile database, Forensic Science International: Genetics, 9 (2014) 102-110.

[3] K. Burham, D. Anderson, Model Selection and Multi-Model Inference: A Practical Information Theoretic Approach, Second Edition, Springer, New York, 2002.

[4] H. Akaike, Information theory as an extension of the maximum likelihood priniciple, in B. N. Petrov and F. Csaki (eds.) Second International Symposium on Information Theory, Akademiai Kiado, Budapest.

[5] N. Suguira, Further analysis of the data by Akaike information criterion and the finite corrections, Communications in Statistics, Theory and Methods, A7, 1978, 13-26.

[6] H. Akaike, Information measures and model selection, International Statistical Institute, 44, 1983, 277-291.

That which is claimed:

1. A method of analyzing a single mixed contributor sample containing DNA where the number of contributors is unknown prior to the analysis of the single mixed contributor sample, the single mixed contributor sample comprising loci within the DNA, the method comprising:

(i) processing the single mixed contributor sample into a plurality of liquid droplets, wherein each of the plurality of liquid droplets contains no more than one locus-containing DNA molecule per targeted locus, wherein isolating the target DNA molecules with the targeted loci in the droplets prevents extended primers from switching between multiple target DNA molecules with different sequences during PCR, thereby preventing creation of chimeric alleles comprising error-containing content due to recombination of genomic content from a plurality of target DNA molecules;

(ii) introducing a plurality of sets of DNA primers into the plurality of liquid droplets, wherein each of the plurality of sets is configured to amplify a different specific locus on a genome, and wherein each of the plurality of sets includes one or more unique molecular tags, and wherein the unique molecular tag(s) of a primer set in one droplet differs from the unique molecular tag(s) of the corresponding primer set in a different droplet;

(iii) subjecting the target DNA molecules in the plurality of liquid droplets to an amplification process comprising a PCR amplification process in the presence of the plurality of sets of DNA primers to provide a plurality of amplicons of targeted DNA sequences at a plurality of pre-determined loci including a first locus, each of the sets of DNA primers being configured to incorporate into the respective plurality of amplicons and thereby append a tag to the plurality of respective amplicons to produce a plurality of sets of uniquely tagged amplicons derived from each of the plurality of targeted DNA sequences, wherein each set of the plurality of sets of uniquely tagged amplicons comprises a respective allelic profile including a first allelic profile comprising error-containing amplicons having DNA sequence errors generated by replication errors of the amplification process and error-free amplicons having no DNA sequence errors, the error-containing amplicons and the error-free amplicons having a same tag;

(iv) sequencing each of the uniquely tagged amplicons to provide at least a first group of sequences having an identical first tag associated with the first locus and a second group of sequences having an identical second tag associated with the first locus; and (v) selecting a first representative DNA sequence from the first group of sequences as representing a first target DNA molecule from the one or more target DNA sequences and selecting a second representative DNA sequence from the second group of sequences as representing a second target DNA molecule;

wherein the first representative DNA sequence is a majority sequence from the first group of sequences and the second representative DNA sequence is a majority sequence from the second group of sequences; and (vi) associating the first representative DNA sequence with a first contributor genotype at the first locus and the second representative DNA sequence with a second contributor genotype at the first locus via performing an Evidence Ratio (ER) analysis derived from Akaike's Information Criterion (AIC) for the first allelic profile that includes the first group of sequences having an identical first tag and the second group of sequences having the identical second tag, the number of DNA contributors at the locus, c, to be inferenced based on the weight of the evidence; wherein the ER analysis derived from the AIC computed for each possible model of the allelic data with 'n' contributors determines the strength of evidence for each possible number of contributors, n, and comprises the following:

$$ER_c^n = \frac{\sum_{m=1}^{r(n)} w_m^*}{\sum_{i \neq n}^{n_{max}} \sum_{m'=1}^{r(i)} w_{m'}^*}$$

wherein 'n' represents the number of contributors;

$w_m^*$ represents each model's Akaike weight as defined in terms of ratios of the model's likelihood (Lm) given the allelic data, where Lm is proportional to $\exp^{(-1/2\Delta m)}$, wherein $\Delta m$ is the difference of the AIC value between model 'm' and a model '$m_{min}$', in which $m_{min}$ has the lowest AIC value and is not zero;

wherein the upper sum in $ER_c^n$ is over a subset r(n) of all possible models with n contributors, and the lower sum is over all possible models with a different number of contributors n', where n' is not equal to n, and $n_{max}$ is the maximum number of contributors considered, with the number of contributors inferenced given by m such that the $ER_c^n$ value is the maximum over all $n_{max}$ considered.

2. The method of claim 1, wherein the processing the single sample into a plurality of liquid droplets comprises forming the plurality of liquid droplets via a droplet microfluidic device.

3. The method of claim 2, wherein a plurality of liquid droplets are used, wherein the plurality of liquid droplets comprises a first group of liquid droplets and a second group of liquid droplets, the first group of liquid droplets being devoid of any DNA molecules and the second group of liquid droplets containing one or more locus-containing DNA molecules, wherein the majority of the second group of liquid droplets contain only one locus-containing DNA molecule per targeted locus.

4. The method of claim 2, wherein one droplet in every 50 to 150 liquid droplets comprises only one locus-containing DNA molecule per targeted locus.

5. The method of claim 2, wherein the average diameter of the plurality of liquid droplets comprises from 1 micron to 100 microns.

6. The method of claim 1, wherein the step of processing the single sample into a plurality of liquid droplets comprises hyper-diluting the single sample and forming the plurality of liquid droplets.

7. The method of claim 6, wherein hyper-diluting the single sample comprises diluting the single sample such that about one liquid droplet for every 50 to 150 liquid droplets includes one locus-containing DNA molecule per targeted locus.

8. The method of claim 1, wherein the DNA primers are encapsulated within non-target-DNA containing liquid droplets formed via a droplet microfluidic device to provide primer-containing liquid droplets, and the step of introducing the one or more sets of DNA primers into the plurality of liquid droplets comprises merging the plurality of liquid droplets with the primer-containing liquid droplets.

9. The method of claim 8, wherein each of the DNA primers is configured to amplify a respective targeted DNA sequence, wherein each respective targeted DNA sequence has a different DNA sequence.

10. The method of claim 9, wherein the DNA primers are affixed to a bead.

11. The method of claim 1, wherein the step of introducing the plurality of sets of DNA primers into the plurality of liquid droplets comprises co-encapsulation of the DNA primers and the one or more locus-containing DNA molecules including a targeted locus via a co-flow microfluidic device whereby the DNA primers and the one or more locus-containing DNA molecules including a targeted locus are encapsulated at the same time.

12. The method of claim 1, wherein the sequencing comprises a next-generation DNA sequencing method.

13. The method of claim 8, wherein the non-target-DNA containing liquid droplets comprise a plurality of sets of DNA primers encapsulated within each droplet, including a first primer set comprising a first tag and a second primer set comprising a second tag; wherein the first tag is different than the second tag.

14. The method of claim 1, wherein the sample comprises a forensic sample, a biological cell sample, a bacterium, a virus, a blood serum fetal genetic screening sample, or a blood serum or resected tumor cancer genetic screening sample.

15. The method of claim 1, wherein DNA sequencing data is used to determine a proportion of minor contributor DNA.

16. The method of claim 1, wherein a number of constituent genomes contributing to the sample is identified by performing an evidence ratio test.

17. The method of claim 1, wherein the first locus is a short tandem repeat (STR).

18. The method of claim 17, wherein the STR is DYS392.

* * * * *

SEQUENCE LISTING

```
<160> NUMBER OF SEQ ID NOS: 2

<210> SEQ ID NO 1
<211> LENGTH: 37
<212> TYPE: DNA
<213> ORGANISM: Homo sapiens

<400> SEQUENCE: 1
tttattatta ttattattat tattattatt attattt                              37

<210> SEQ ID NO 2
<211> LENGTH: 43
<212> TYPE: DNA
<213> ORGANISM: Homo sapiens

<400> SEQUENCE: 2
tttattatta ttattattat tattattatt attattatta ttt                       43
```